(12) United States Patent
Fishman et al.

(10) Patent No.: US 6,919,079 B1
(45) Date of Patent: Jul. 19, 2005

(54) FCεPE CHIMERIC PROTEIN FOR TARGETED TREATMENT OF ALLERGY RESPONSES, A METHOD FOR ITS PRODUCTION AND PHARMACEUTICAL COMPOSITIONS CONTAINING THE SAME

(75) Inventors: Ala Fishman, Haita (IL); Shai Yarkoni, Kfar-Saba (IL); Haya Lorberboumgalski, Jerusalem (IL)

(73) Assignee: Yissum Research Company of the Hebrew University of Jerusalem (IL)

( * ) Notice: Subject to any disclaimer, the term of this patent is extended or adjusted under 35 U.S.C. 154(b) by 0 days.

(21) Appl. No.: 09/091,645

(22) PCT Filed: Dec. 18, 1996

(86) PCT No.: PCT/IL96/00181

§ 371 (c)(1),
(2), (4) Date: Jun. 18, 1998

(87) PCT Pub. No.: WO97/22364

PCT Pub. Date: Jun. 26, 1997

(30) Foreign Application Priority Data

Dec. 18, 1995 (IL) ................................................ 116436

(51) Int. Cl.[7] ........................................... A61K 39/395
(52) U.S. Cl. ................................ 424/183.1; 424/144.1; 424/193.1; 424/197.11; 530/388.22; 530/391.7
(58) Field of Search .................... 424/197.11, 144.1, 424/193.1, 183.1; 530/388.22, 391.1

(56) References Cited

U.S. PATENT DOCUMENTS 5,082,927 A    1/1992   Fitzgerald

FOREIGN PATENT DOCUMENTS

| WO | WO 88/00204 | * | 1/1988 |
| WO | WO 9012592 |   | 11/1990 |
| WO | WO 9111456 |   | 8/1991 |
| WO | WO 9404689 |   | 3/1994 |

OTHER PUBLICATIONS

Boltansky et al. Immunopharmacology, vol. 14(1) pp. 47–62, 1987.*
Kondo et al. J.B.C. vol. 263(19), 9470–9475, 1988.*

Nature, vol. 331, Jan. 14, 1988, pp. 180–183, Helm et al., "The mast cell binding site on human immunoglobulin E".
The Journal of Immuonololgy, vol. 140, No. 8, Apr. 15, 1988, pp. 2585–2588, Kitani et al., "Inhibition of Allergic Reactions with Monoclonal Antibody to the High Affinity IgE Receptor".
Nature, vol. 339, No. 6223, Jun. 1, 1989, pp. 394–397, Chaudhary V. K. et al., "A recombinant immunotoxin consisting of two antibody variable domains fused to pseudomonas exotoxin."
The Journal of Biological Chemistry, vol. 263, No. 19, Jul. 5, 1988, pp. 9470–9475, Kondo et al., "Activity of Immunotoxins Constructed With Modified Pseudomonas Exotoxin a Lacking the Cell Recognition Domain".

* cited by examiner

Primary Examiner—Patrick J. Nolan
(74) Attorney, Agent, or Firm—Lowe Hauptman Gilman & Berner LLP

(57) ABSTRACT

The present invention generally relates to a new approach for the therapy of allergic responses, based on targeted elimination of cells expressing the FcεRI receptor by a chimeric cytotoxin $Fc_{2'-3}$-$PE_{40}$. A sequence encoding amino acids 301–437 of the Fc region of the mouse IgE molecule was genetically fused to $PE_{40}$—a truncated form of PE lacking the cell binding domain. The chimeric protein, produced in E. coli, specifically and efficiently kills mouse mast cell lines expressing the FcεRI receptor, as well as primary mast cells derived from bone marrow. The present invention provides a chimeric protein for targeted elimination of $Fc_εRI$ expressing cells especially useful for the therapy of allergic responses. The said chimeric protein is comprised of a cell targeting moiety for $Fc_εRI$ expressing cells and a cell killing moiety. The preferred killing moiety is the bacterial toxin Pseudomonas exotoxin (PE). This Pseudomonas exotoxin is a product of *Pseudomonas aeruginosa*. The present invention also relates to a method for the preparation of said protein. This chimeric protein is prepared by genetically fusing the Fc region of the mouse IgE molecule to $PE_{40}$, a truncated form of PE lacking the cell binding domain. The present invention also provides pharmaceutical compositions, for the treatment of allergic diseases and for the treatment of hyperplasias and malignancies, comprising as an active ingredient the above mentioned chimeric protein and a conventional adjuvant product.

7 Claims, 18 Drawing Sheets

Sequence ID No. 1

Sequence ID No. 3

Cytotoxicity of $Fc_{2'-3}$-$PE_{40}$ chimeric protein against various mouse cells

|  |  | Cell line | Cell Origin | $ID_{50}$ (ng/ml) |
|---|---|---|---|---|
| TARGET CELLS | | MC-9 | Mast cells | 50-100 |
| | | C57 | Mast cells | 100-125 |
| | | BMMC | Primary bone marrow-derived mast cells | |
| | | Abelson | Transformed mast cells | 1,200-1,500 |
| NON-TARGET CELLS | HEMOPOETIC | $L_{10}A$ | B cell, non-secreting | > 10,000 |
| | | $X_{16}B$ | B cell, non-secreting | > 10,000 |
| | | UT | B cell, non-secreting | > 10,000 |
| | | PD1.1 | T cell, immature | > 10,000 |
| | | EL-4 | T cell, mature | > 10,000 |
| | | Erythro-leukemia | | > 10,000 |
| | CONNECTIVE TISSUE | L TK | Fibroblast | 1900 |
| | | Hepatoma | | 1500 |

Figure 13

SEQUENCE LISTING

```
<160> NUMBER OF SEQ ID NOS: 8

<210> SEQ ID NO 1
<211> LENGTH: 2031
<212> TYPE: DNA
<213> ORGANISM: mouse
<220> FEATURE:
<221> NAME/KEY: CDS
<222> LOCATION: (1)..(1512)
<223> OTHER INFORMATION: 1. The mouse IgE constant region (=F(Ce))
      2. Pseudomonas aeruginosa Endotoxin (PE40)

<400> SEQUENCE: 1 atg cga cct gtc aac atc act gag ccc acc ttg gag cta ctc cat tca      48
Met Arg Pro Val Asn Ile Thr Glu Pro Thr Leu Glu Leu Leu His Ser
1               5                   10                  15 tcc tgc gac ccc aat gca ttc cac tcc acc atc cag ctg tac tgc ttc      96
Ser Cys Asp Pro Asn Ala Phe His Ser Thr Ile Gln Leu Tyr Cys Phe
                20                  25                  30 att tat ggc cac atc cta aat gat gtc tct gtc agc tgg cta atg gac     144
Ile Tyr Gly His Ile Leu Asn Asp Val Ser Val Ser Trp Leu Met Asp
            35                  40                  45 gat cgg gag ata act gat aca ctt gca caa act gtt cta atc aag gag     192
Asp Arg Glu Ile Thr Asp Thr Leu Ala Gln Thr Val Leu Ile Lys Glu
        50                  55                  60 gaa ggc aaa cta gcc tct acc tgc agt aaa ctc aac atc act gag cag     240
Glu Gly Lys Leu Ala Ser Thr Cys Ser Lys Leu Asn Ile Thr Glu Gln
65                  70                  75                  80 caa tgg atg tct gaa agc acc ttc acc tgc aag gtc acc tcc caa ggc     288
Gln Trp Met Ser Glu Ser Thr Phe Thr Cys Lys Val Thr Ser Gln Gly
                85                  90                  95 gta gac tat ttg gcc cac act cgg aga tgc cca gat cat gag cca cgg     336
Val Asp Tyr Leu Ala His Thr Arg Arg Cys Pro Asp His Glu Pro Arg
                100                 105                 110 ggt gtg att acc tac ctg atc cca ccc agc ccc ctg gac ctg tat caa     384
Gly Val Ile Thr Tyr Leu Ile Pro Pro Ser Pro Leu Asp Leu Tyr Gln
            115                 120                 125 aac ggt gct ccc aag ctt acc tgt ctg gtg gtg gac ctg gaa agc gag     432
Asn Gly Ala Pro Lys Leu Thr Cys Leu Val Val Asp Leu Glu Ser Glu
        130                 135                 140 aag aat gtc aat gtg acg tgg aac caa gag aag aag act tca gtc tca     480
Lys Asn Val Asn Val Thr Trp Asn Gln Glu Lys Lys Thr Ser Val Ser
145                 150                 155                 160 gca tcc cag tgg tac act aag cac cac aat aac ggc aca act agt atc     528
```

```
Ala Ser Gln Trp Tyr Thr Lys His His Asn Asn Gly Thr Thr Ser Ile
            165                 170                 175 acc tcc atc ctg cct gta gtt gcc aag gac tgg att gaa ggc tac ggc       576
Thr Ser Ile Leu Pro Val Val Ala Lys Asp Trp Ile Glu Gly Tyr Gly
        180                 185                 190 tat cag tgc ata gtg gac cac cct gat ttt ccc aag ccc att gtg cgt       624
Tyr Gln Cys Ile Val Asp His Pro Asp Phe Pro Lys Pro Ile Val Arg
            195                 200                 205 tcc atc acc aag acc cca ggc cag cgc tca gcc ccc gag gta tat gtg       672
Ser Ile Thr Lys Thr Pro Gly Gln Arg Ser Ala Pro Glu Val Tyr Val
        210                 215                 220 ttc cca cca cca gag gag gag agc gag gac aaa cgc aca ctc acc tgt       720
Phe Pro Pro Pro Glu Glu Glu Ser Glu Asp Lys Arg Thr Leu Thr Cys
225                 230                 235                 240 ttg atc cag aac ttc ttc cct gag gat atc tct gtg cag tgg ctg ggg       768
Leu Ile Gln Asn Phe Phe Pro Glu Asp Ile Ser Val Gln Trp Leu Gly
                245                 250                 255 gat ggc aaa ctg atc tca aac agc cag cac agt acc aca aca ccc ctg       816
Asp Gly Lys Leu Ile Ser Asn Ser Gln His Ser Thr Thr Thr Pro Leu
            260                 265                 270 aaa tcc aat ggc tcc aat caa ggc ttc ttc atc ttc agt cgc cta gag       864
Lys Ser Asn Gly Ser Asn Gln Gly Phe Phe Ile Phe Ser Arg Leu Glu
        275                 280                 285 gtc gcc aag aca ctc tgg aca cag aga aaa cag ttc acc tgc caa gtg       912
Val Ala Lys Thr Leu Trp Thr Gln Arg Lys Gln Phe Thr Cys Gln Val
    290                 295                 300 atc cat gag gca ctt cag cat atg gcc gaa gag ggc ggc agc ctg gcc       960
Ile His Glu Ala Leu Gln His Met Ala Glu Glu Gly Gly Ser Leu Ala
305                 310                 315                 320 gcg ctg acc gcg cac cag gct tgc cac ctg ccg ctg gag act ttc acc      1008
Ala Leu Thr Ala His Gln Ala Cys His Leu Pro Leu Glu Thr Phe Thr
                325                 330                 335 cgt cat cgc cag ccg cgc ggc tgg gaa caa ctg gag cag tgc ggc tat      1056
Arg His Arg Gln Pro Arg Gly Trp Glu Gln Leu Glu Gln Cys Gly Tyr
            340                 345                 350 ccg gtg cag cgg ctg gtc gcc ctc tac ctg gcg gcg cgg ctg tcg tgg      1104
Pro Val Gln Arg Leu Val Ala Leu Tyr Leu Ala Ala Arg Leu Ser Trp
        355                 360                 365 aac cag gtc gac cag gtg atc cgc aac gcc ctg gcc agc ccc ggc agc      1152
Asn Gln Val Asp Gln Val Ile Arg Asn Ala Leu Ala Ser Pro Gly Ser
    370                 375                 380 ggc ggc agc ctg ggc gaa gcg atc cgc gag cag ccg gag cag gcc cgt      1200
Gly Gly Ser Leu Gly Glu Ala Ile Arg Glu Gln Pro Glu Gln Ala Arg
385                 390                 395                 400 ctg gcc ctg acc ctg gcc gcc gcc gag agc gag cgc ttc gtc cgg cag      1248
Leu Ala Leu Thr Leu Ala Ala Ala Glu Ser Glu Arg Phe Val Arg Gln
                405                 410                 415 ggc acc ggc aac gac gag gcc ggc gcg gcc aac gcc gac gtg gtg agc      1296
Gly Thr Gly Asn Asp Glu Ala Gly Ala Ala Asn Ala Asp Val Val Ser
            420                 425                 430 ctg acc tgc ccg gtc gcc gcc ggt gaa tgc gcg ggc ccg gcg gac agc      1344
Leu Thr Cys Pro Val Ala Ala Gly Glu Cys Ala Gly Pro Ala Asp Ser
        435                 440                 445 ggc gac gcc ctg ctg gag cgc aac tat ccc act ggc gcg gag ttc ctc      1392
Gly Asp Ala Leu Leu Glu Arg Asn Tyr Pro Thr Gly Ala Glu Phe Leu
    450                 455                 460 ggc gac ggc ggc gac gtc agc ttc agc acc cgc ggc acg cag aac tgg      1440
Gly Asp Gly Gly Asp Val Ser Phe Ser Thr Arg Gly Thr Gln Asn Trp
465                 470                 475                 480
```

```
acg gtg gag cgg ctg ctc cag gcg cac cgc caa ctg gag gag cgc ggc         1488
Thr Val Glu Arg Leu Leu Gln Ala His Arg Gln Leu Glu Glu Arg Gly
            485                 490                 495 tat gtg ttc gtc ggc tac cac ggc accttcctcg aagcggcgca aagcatcgtc         1542
Tyr Val Phe Val Gly Tyr His Gly
                500 ttcggcgggg tgcgcgcgcg cagccaggac ctcgacgcga tctggcgcgg tttctatatc         1602 gccggcgatc cggcgctggc ctacggctac gcccaggacc aggaacccga cgcacgcggc         1662 cggatccgca acgtgccct gctgcgggtc tatgtgccgc gctcgagcct gccgggcttc          1722 taccgcacca gcctgaccct ggccgcgccg gaggcggcgg cgaggtcga acggctgatc          1782 ggccatccgc tgccgctgcg cctggacgcc atcaccggcc ccgaggagga aggcgggcgc         1842 ctggagacca ttctcggctg gccgctggcc gagcgcaccg tggtgattcc ctcggcgatc         1902 cccaccgacc cgcgcaacgt cggcggcgac ctcgacccgt ccagcatccc cgacaaggaa         1962 caggcgatca cgcccctgcc ggactacgcc agccagcccg gcaaaccgcc gcgcgaggac         2022 ctgaagtaa                                                                 2031

<210> SEQ ID NO 2
<211> LENGTH: 504
<212> TYPE: PRT
<213> ORGANISM: mouse

<400> SEQUENCE: 2

Met Arg Pro Val Asn Ile Thr Glu Pro Thr Leu Glu Leu Leu His Ser
1               5                   10                  15

Ser Cys Asp Pro Asn Ala Phe His Ser Thr Ile Gln Leu Tyr Cys Phe
                20                  25                  30

Ile Tyr Gly His Ile Leu Asn Asp Val Ser Val Ser Trp Leu Met Asp
            35                  40                  45

Asp Arg Glu Ile Thr Asp Thr Leu Ala Gln Thr Val Leu Ile Lys Glu
        50                  55                  60

Glu Gly Lys Leu Ala Ser Thr Cys Ser Lys Leu Asn Ile Thr Glu Gln
65                  70                  75                  80

Gln Trp Met Ser Glu Ser Thr Phe Thr Cys Lys Val Thr Ser Gln Gly
                85                  90                  95

Val Asp Tyr Leu Ala His Thr Arg Arg Cys Pro Asp His Glu Pro Arg
            100                 105                 110

Gly Val Ile Thr Tyr Leu Ile Pro Pro Ser Pro Leu Asp Leu Tyr Gln
        115                 120                 125

Asn Gly Ala Pro Lys Leu Thr Cys Leu Val Val Asp Leu Glu Ser Glu
    130                 135                 140

Lys Asn Val Asn Val Thr Trp Asn Gln Glu Lys Lys Thr Ser Val Ser
145                 150                 155                 160

Ala Ser Gln Trp Tyr Thr Lys His His Asn Asn Gly Thr Thr Ser Ile
                165                 170                 175

Thr Ser Ile Leu Pro Val Val Ala Lys Asp Trp Ile Glu Gly Tyr Gly
            180                 185                 190

Tyr Gln Cys Ile Val Asp His Pro Asp Phe Pro Lys Pro Ile Val Arg
        195                 200                 205

Ser Ile Thr Lys Thr Pro Gly Gln Arg Ser Ala Pro Glu Val Tyr Val
    210                 215                 220

Phe Pro Pro Pro Glu Glu Glu Ser Glu Asp Lys Arg Thr Leu Thr Cys
225                 230                 235                 240
```

-continued

```
Leu Ile Gln Asn Phe Phe Pro Glu Asp Ile Ser Val Gln Trp Leu Gly
            245                 250                 255
Asp Gly Lys Leu Ile Ser Asn Ser Gln His Ser Thr Thr Thr Pro Leu
            260                 265                 270
Lys Ser Asn Gly Ser Asn Gln Gly Phe Phe Ile Phe Ser Arg Leu Glu
            275                 280                 285
Val Ala Lys Thr Leu Trp Thr Gln Arg Lys Gln Phe Thr Cys Gln Val
            290                 295                 300
Ile His Glu Ala Leu Gln His Met Ala Glu Glu Gly Ser Leu Ala
305                 310                 315                 320
Ala Leu Thr Ala His Gln Ala Cys His Leu Pro Leu Glu Thr Phe Thr
            325                 330                 335
Arg His Arg Gln Pro Arg Gly Trp Glu Gln Leu Glu Gln Cys Gly Tyr
            340                 345                 350
Pro Val Gln Arg Leu Val Ala Leu Tyr Leu Ala Ala Arg Leu Ser Trp
            355                 360                 365
Asn Gln Val Asp Gln Val Ile Arg Asn Ala Leu Ala Ser Pro Gly Ser
            370                 375                 380
Gly Gly Ser Leu Gly Glu Ala Ile Arg Glu Gln Pro Glu Gln Ala Arg
385                 390                 395                 400
Leu Ala Leu Thr Leu Ala Ala Ala Glu Ser Glu Arg Phe Val Arg Gln
            405                 410                 415
Gly Thr Gly Asn Asp Glu Ala Gly Ala Ala Asn Ala Asp Val Val Ser
            420                 425                 430
Leu Thr Cys Pro Val Ala Ala Gly Glu Cys Ala Gly Pro Ala Asp Ser
            435                 440                 445
Gly Asp Ala Leu Leu Glu Arg Asn Tyr Pro Thr Gly Ala Glu Phe Leu
450                 455                 460
Gly Asp Gly Gly Asp Val Ser Phe Ser Thr Arg Gly Thr Gln Asn Trp
465                 470                 475                 480
Thr Val Glu Arg Leu Leu Gln Ala His Arg Gln Leu Glu Glu Arg Gly
            485                 490                 495
Tyr Val Phe Val Gly Tyr His Gly
            500
```

<210> SEQ ID NO 3
<211> LENGTH: 2031
<212> TYPE: DNA
<213> ORGANISM: Pseudomonas aeruginosa
<220> FEATURE:
<221> NAME/KEY: CDS
<222> LOCATION: (1)..(2031)
<223> OTHER INFORMATION: 1. The mouse IgE constant region (=F(Ce))
    2. Pseudomonas aeruginosa Endotoxin (PE40)

<400> SEQUENCE: 3

```
atg cga cct gtc aac atc act gag ccc acc ttg gag cta ctc cat tca    48
Met Arg Pro Val Asn Ile Thr Glu Pro Thr Leu Glu Leu Leu His Ser
1               5                   10                  15 tcc tgc gac ccc aat gca ttc cac tcc acc atc cag ctg tac tgc ttc    96
Ser Cys Asp Pro Asn Ala Phe His Ser Thr Ile Gln Leu Tyr Cys Phe
                20                  25                  30 att tat ggc cac atc cta aat gat gtc tct gtc agc tgg cta atg gac   144
Ile Tyr Gly His Ile Leu Asn Asp Val Ser Val Ser Trp Leu Met Asp
            35                  40                  45 gat cgg gag ata act gat aca ctt gca caa act gtt cta atc aag gag   192
Asp Arg Glu Ile Thr Asp Thr Leu Ala Gln Thr Val Leu Ile Lys Glu
50                  55                  60
```

-continued

```
gaa ggc aaa cta gcc tct acc tgc agt aaa ctc aac atc act gag cag      240
Glu Gly Lys Leu Ala Ser Thr Cys Ser Lys Leu Asn Ile Thr Glu Gln
 65              70                  75                  80 caa tgg atg tct gaa agc acc ttc acc tgc aag gtc acc tcc caa ggc      288
Gln Trp Met Ser Glu Ser Thr Phe Thr Cys Lys Val Thr Ser Gln Gly
                 85                  90                  95 gta gac tat ttg gcc cac act cgg aga tgc cca gat cat gag cca cgg      336
Val Asp Tyr Leu Ala His Thr Arg Arg Cys Pro Asp His Glu Pro Arg
            100                 105                 110 ggt gtg att acc tac ctg atc cca ccc agc ccc ctg gac ctg tat caa      384
Gly Val Ile Thr Tyr Leu Ile Pro Pro Ser Pro Leu Asp Leu Tyr Gln
        115                 120                 125 aac ggt gct ccc aag ctt acc tgt ctg gtg gtg gac ctg gaa agc gag      432
Asn Gly Ala Pro Lys Leu Thr Cys Leu Val Val Asp Leu Glu Ser Glu
130                 135                 140 aag aat gtc aat gtg acg tgg aac caa gag aag aag act tca gtc tca      480
Lys Asn Val Asn Val Thr Trp Asn Gln Glu Lys Lys Thr Ser Val Ser
145                 150                 155                 160 gca tcc cag tgg tac act aag cac cac aat aac ggc aca act agt atc      528
Ala Ser Gln Trp Tyr Thr Lys His His Asn Asn Gly Thr Thr Ser Ile
                165                 170                 175 acc tcc atc ctg cct gta gtt gcc aag gac tgg att gaa ggc tac ggc      576
Thr Ser Ile Leu Pro Val Val Ala Lys Asp Trp Ile Glu Gly Tyr Gly
            180                 185                 190 tat cag tgc ata gtg gac cac cct gat ttt ccc aag ccc att gtg cgt      624
Tyr Gln Cys Ile Val Asp His Pro Asp Phe Pro Lys Pro Ile Val Arg
        195                 200                 205 tcc atc acc aag acc cca ggc cag cgc tca gcc ccc gag gta tat gtg      672
Ser Ile Thr Lys Thr Pro Gly Gln Arg Ser Ala Pro Glu Val Tyr Val
210                 215                 220 ttc cca cca cca gag gag gag agc gag gac aaa cgc aca ctc acc tgt      720
Phe Pro Pro Pro Glu Glu Glu Ser Glu Asp Lys Arg Thr Leu Thr Cys
225                 230                 235                 240 ttg atc cag aac ttc ttc cct gag gat atc tct gtg cag tgg ctg ggg      768
Leu Ile Gln Asn Phe Phe Pro Glu Asp Ile Ser Val Gln Trp Leu Gly
                245                 250                 255 gat ggc aaa ctg atc tca aac agc cag cac agt acc aca aca ccc ctg      816
Asp Gly Lys Leu Ile Ser Asn Ser Gln His Ser Thr Thr Thr Pro Leu
            260                 265                 270 aaa tcc aat ggc tcc aat caa ggc ttc ttc atc ttc agt cgc cta gag      864
Lys Ser Asn Gly Ser Asn Gln Gly Phe Phe Ile Phe Ser Arg Leu Glu
        275                 280                 285 gtc gcc aag aca ctc tgg aca cag aga aaa cag ttc acc tgc caa gtg      912
Val Ala Lys Thr Leu Trp Thr Gln Arg Lys Gln Phe Thr Cys Gln Val
290                 295                 300 atc cat gag gca ctt cag cat atg gcc gaa gag ggc ggc agc ctg gcc      960
Ile His Glu Ala Leu Gln His Met Ala Glu Glu Gly Gly Ser Leu Ala
305                 310                 315                 320 gcg ctg acc gcg cac cag gct tgc cac ctg ccg ctg gag act ttc acc     1008
Ala Leu Thr Ala His Gln Ala Cys His Leu Pro Leu Glu Thr Phe Thr
                325                 330                 335 cgt cat cgc cag ccg cgc ggc tgg gaa caa ctg gag cag tgc ggc tat     1056
Arg His Arg Gln Pro Arg Gly Trp Glu Gln Leu Glu Gln Cys Gly Tyr
            340                 345                 350 ccg gtg cag cgg ctg gtc gcc ctc tac ctg gcg gcg cgg ctg tcg tgg     1104
Pro Val Gln Arg Leu Val Ala Leu Tyr Leu Ala Ala Arg Leu Ser Trp
        355                 360                 365 aac cag gtc gac cag gtg atc cgc aac gcc ctg gcc agc ccc ggc agc     1152
Asn Gln Val Asp Gln Val Ile Arg Asn Ala Leu Ala Ser Pro Gly Ser
```

-continued

| | |
|---|---|
| ggc ggc agc ctg ggc gaa gcg atc cgc gag cag ccg gag cag gcc cgt<br>Gly Gly Ser Leu Gly Glu Ala Ile Arg Glu Gln Pro Glu Gln Ala Arg<br>385               390               395               400 | 1200 |
| ctg gcc ctg acc ctg gcc gcc gcc gag agc gag cgc ttc gtc cgg cag<br>Leu Ala Leu Thr Leu Ala Ala Ala Glu Ser Glu Arg Phe Val Arg Gln<br>               405               410               415 | 1248 |
| ggc acc ggc aac gac gag gcc ggc gcg gcc aac gcc gac gtg gtg agc<br>Gly Thr Gly Asn Asp Glu Ala Gly Ala Ala Asn Ala Asp Val Val Ser<br>420               425               430 | 1296 |
| ctg acc tgc ccg gtc gcc gcc ggt gaa tgc gcg ggc ccg gcg gac agc<br>Leu Thr Cys Pro Val Ala Ala Gly Glu Cys Ala Gly Pro Ala Asp Ser<br>          435               440               445 | 1344 |
| ggc gac gcc ctg ctg gag cgc aac tat ccc act ggc gcg gag ttc ctc<br>Gly Asp Ala Leu Leu Glu Arg Asn Tyr Pro Thr Gly Ala Glu Phe Leu<br>450               455               460 | 1392 |
| ggc gac ggc ggc gac gtc agc ttc agc acc cgc ggc acg cag aac tgg<br>Gly Asp Gly Gly Asp Val Ser Phe Ser Thr Arg Gly Thr Gln Asn Trp<br>465               470               475               480 | 1440 |
| acg gtg gag cgg ctg ctc cag gcg cac cgc caa ctg gag gag cgc ggc<br>Thr Val Glu Arg Leu Leu Gln Ala His Arg Gln Leu Glu Glu Arg Gly<br>               485               490               495 | 1488 |
| tat gtg ttc gtc ggc tac cac ggc acc ttc ctc gaa gcg gcg caa agc<br>Tyr Val Phe Val Gly Tyr His Gly Thr Phe Leu Glu Ala Ala Gln Ser<br>500               505               510 | 1536 |
| atc gtc ttc ggc ggg gtg cgc gcg cgc agc cag gac ctc gac gcg atc<br>Ile Val Phe Gly Gly Val Arg Ala Arg Ser Gln Asp Leu Asp Ala Ile<br>          515               520               525 | 1584 |
| tgg cgc ggt ttc tat atc gcc ggc gat ccg gcg ctg gcc tac ggc tac<br>Trp Arg Gly Phe Tyr Ile Ala Gly Asp Pro Ala Leu Ala Tyr Gly Tyr<br>530               535               540 | 1632 |
| gcc cag gac cag gaa ccc gac gca cgc ggc cgg atc cgc aac ggt gcc<br>Ala Gln Asp Gln Glu Pro Asp Ala Arg Gly Arg Ile Arg Asn Gly Ala<br>545               550               555               560 | 1680 |
| ctg ctg cgg gtc tat gtg ccg cgc tcg agc ctg ccg ggc ttc tac cgc<br>Leu Leu Arg Val Tyr Val Pro Arg Ser Ser Leu Pro Gly Phe Tyr Arg<br>               565               570               575 | 1728 |
| acc agc ctg acc ctg gcc gcg ccg gag gcg gcg ggc gag gtc gaa cgg<br>Thr Ser Leu Thr Leu Ala Ala Pro Glu Ala Ala Gly Glu Val Glu Arg<br>580               585               590 | 1776 |
| ctg atc ggc cat ccg ctg ccg ctg cgc ctg gac gcc atc acc ggc ccc<br>Leu Ile Gly His Pro Leu Pro Leu Arg Leu Asp Ala Ile Thr Gly Pro<br>          595               600               605 | 1824 |
| gag gag gaa ggc ggg cgc ctg gag acc att ctc ggc tgg ccg ctg gcc<br>Glu Glu Glu Gly Gly Arg Leu Glu Thr Ile Leu Gly Trp Pro Leu Ala<br>610               615               620 | 1872 |
| gag cgc acc gtg gtg att ccc tcg gcg atc ccc acc gac ccg cgc aac<br>Glu Arg Thr Val Val Ile Pro Ser Ala Ile Pro Thr Asp Pro Arg Asn<br>625               630               635               640 | 1920 |
| gtc ggc ggc gac ctc gac ccg tcc agc atc ccc gac aag gaa cag gcg<br>Val Gly Gly Asp Leu Asp Pro Ser Ser Ile Pro Asp Lys Glu Gln Ala<br>               645               650               655 | 1968 |
| atc agc gcc ctg ccg gac tac gcc agc cag ccc ggc aaa ccg ccg cgc<br>Ile Ser Ala Leu Pro Asp Tyr Ala Ser Gln Pro Gly Lys Pro Pro Arg<br>660               665               670 | 2016 |
| gag gac ctg aag taa<br>Glu Asp Leu Lys<br>675 | 2031 |

<210> SEQ ID NO 4
<211> LENGTH: 676
<212> TYPE: PRT
<213> ORGANISM: Pseudomonas aeruginosa

<400> SEQUENCE: 4

```
Met Arg Pro Val Asn Ile Thr Glu Pro Thr Leu Glu Leu Leu His Ser
1               5                   10                  15

Ser Cys Asp Pro Asn Ala Phe His Ser Thr Ile Gln Leu Tyr Cys Phe
            20                  25                  30

Ile Tyr Gly His Ile Leu Asn Asp Val Ser Val Ser Trp Leu Met Asp
        35                  40                  45

Asp Arg Glu Ile Thr Asp Thr Leu Ala Gln Thr Val Leu Ile Lys Glu
    50                  55                  60

Glu Gly Lys Leu Ala Ser Thr Cys Ser Lys Leu Asn Ile Thr Glu Gln
65                  70                  75                  80

Gln Trp Met Ser Glu Ser Thr Phe Thr Cys Lys Val Thr Ser Gln Gly
                85                  90                  95

Val Asp Tyr Leu Ala His Thr Arg Arg Cys Pro Asp His Glu Pro Arg
            100                 105                 110

Gly Val Ile Thr Tyr Leu Ile Pro Pro Ser Pro Leu Asp Leu Tyr Gln
        115                 120                 125

Asn Gly Ala Pro Lys Leu Thr Cys Leu Val Val Asp Leu Glu Ser Glu
    130                 135                 140

Lys Asn Val Asn Val Thr Trp Asn Gln Glu Lys Lys Thr Ser Val Ser
145                 150                 155                 160

Ala Ser Gln Trp Tyr Thr Lys His His Asn Asn Gly Thr Thr Ser Ile
                165                 170                 175

Thr Ser Ile Leu Pro Val Val Ala Lys Asp Trp Ile Glu Gly Tyr Gly
            180                 185                 190

Tyr Gln Cys Ile Val Asp His Pro Asp Phe Pro Lys Pro Ile Val Arg
        195                 200                 205

Ser Ile Thr Lys Thr Pro Gly Gln Arg Ser Ala Pro Glu Val Tyr Val
    210                 215                 220

Phe Pro Pro Pro Glu Glu Glu Ser Glu Asp Lys Arg Thr Leu Thr Cys
225                 230                 235                 240

Leu Ile Gln Asn Phe Phe Pro Glu Asp Ile Ser Val Gln Trp Leu Gly
                245                 250                 255

Asp Gly Lys Leu Ile Ser Asn Ser Gln His Ser Thr Thr Thr Pro Leu
            260                 265                 270

Lys Ser Asn Gly Ser Asn Gln Gly Phe Phe Ile Phe Ser Arg Leu Glu
        275                 280                 285

Val Ala Lys Thr Leu Trp Thr Gln Arg Lys Gln Phe Thr Cys Gln Val
    290                 295                 300

Ile His Glu Ala Leu Gln His Met Ala Glu Glu Gly Gly Ser Leu Ala
305                 310                 315                 320

Ala Leu Thr Ala His Gln Ala Cys His Leu Pro Leu Glu Thr Phe Thr
                325                 330                 335

Arg His Arg Gln Pro Arg Gly Trp Glu Gln Leu Glu Gln Cys Gly Tyr
            340                 345                 350

Pro Val Gln Arg Leu Val Ala Leu Tyr Leu Ala Ala Arg Leu Ser Trp
        355                 360                 365

Asn Gln Val Asp Gln Val Ile Arg Asn Ala Leu Ala Ser Pro Gly Ser
    370                 375                 380
```

-continued

```
Gly Gly Ser Leu Gly Glu Ala Ile Arg Glu Gln Pro Glu Gln Ala Arg
385                 390                 395                 400
Leu Ala Leu Thr Leu Ala Ala Glu Ser Glu Arg Phe Val Arg Gln
            405                 410                 415
Gly Thr Gly Asn Asp Glu Ala Gly Ala Ala Asn Ala Asp Val Val Ser
                420                 425                 430
Leu Thr Cys Pro Val Ala Ala Gly Glu Cys Ala Gly Pro Ala Asp Ser
            435                 440                 445
Gly Asp Ala Leu Leu Glu Arg Asn Tyr Pro Thr Gly Ala Glu Phe Leu
        450                 455                 460
Gly Asp Gly Gly Asp Val Ser Phe Ser Thr Arg Gly Thr Gln Asn Trp
465                 470                 475                 480
Thr Val Glu Arg Leu Leu Gln Ala His Arg Gln Leu Glu Glu Arg Gly
                485                 490                 495
Tyr Val Phe Val Gly Tyr His Gly Thr Phe Leu Glu Ala Ala Gln Ser
            500                 505                 510
Ile Val Phe Gly Gly Val Arg Ala Arg Ser Gln Asp Leu Asp Ala Ile
        515                 520                 525
Trp Arg Gly Phe Tyr Ile Ala Gly Asp Pro Ala Leu Ala Tyr Gly Tyr
530                 535                 540
Ala Gln Asp Gln Glu Pro Asp Ala Arg Gly Arg Ile Arg Asn Gly Ala
545                 550                 555                 560
Leu Leu Arg Val Tyr Val Pro Arg Ser Ser Leu Pro Gly Phe Tyr Arg
                565                 570                 575
Thr Ser Leu Thr Leu Ala Ala Pro Glu Ala Ala Gly Glu Val Glu Arg
            580                 585                 590
Leu Ile Gly His Pro Leu Pro Leu Arg Leu Asp Ala Ile Thr Gly Pro
        595                 600                 605
Glu Glu Glu Gly Gly Arg Leu Glu Thr Ile Leu Gly Trp Pro Leu Ala
610                 615                 620
Glu Arg Thr Val Val Ile Pro Ser Ala Ile Pro Thr Asp Pro Arg Asn
625                 630                 635                 640
Val Gly Gly Asp Leu Asp Pro Ser Ser Ile Pro Asp Lys Glu Gln Ala
                645                 650                 655
Ile Ser Ala Leu Pro Asp Tyr Ala Ser Gln Pro Gly Lys Pro Pro Arg
            660                 665                 670
Glu Asp Leu Lys
        675

<210> SEQ ID NO 5
<211> LENGTH: 30
<212> TYPE: DNA
<213> ORGANISM: Synthetic Oligonucleotide

<400> SEQUENCE: 5
gcggatccca tatggagcaa tggatgtcgt                                    30

<210> SEQ ID NO 6
<211> LENGTH: 33
<212> TYPE: DNA
<213> ORGANISM: Synthetic Oligonucleotide

<400> SEQUENCE: 6
gcggatccca tatgtggggt cttggtgatg aa                                 33

<210> SEQ ID NO 7
```

```
<211> LENGTH: 33
<212> TYPE: DNA
<213> ORGANISM: Synthetic Oligonucleotide

<400> SEQUENCE: 7
gcggatccca tatgcgacct gtcaacatca ctg                                    33

<210> SEQ ID NO 8
<211> LENGTH: 30
<212> TYPE: DNA
<213> ORGANISM: Synthetic Oligonucleotide

<400> SEQUENCE: 8
gcggatccca tatgggaggg acggagggag                                        30
```

FCεPE CHIMERIC PROTEIN FOR TARGETED TREATMENT OF ALLERGY RESPONSES, A METHOD FOR ITS PRODUCTION AND PHARMACEUTICAL COMPOSITIONS CONTAINING THE SAME

FIELD OF THE INVENTION

The present invention generally relates to a novel approach for the therapy of allergic responses. More specifically the present invention relates to Fcε-PE chimeric protein for targeted elimination of $Fc_\epsilon RI$ expressing cells, a method for its production, and pharmaceutical compositions containing the same. This chimeric protein is composed of cell targeting which is a part of IgE molecule linked to cell killing moieties for recognizing and distroying cells overexpressing the specific receptor. The killing moiety used in the chimeric protein of the present invention is the bacterial toxin Pseudomonas exotoxin (PE) (a product of *Pseudomonas aeruginosa*).

BACKGROUND OF THE INVENTION

About twenty percent of the world population suffers from various allergic diseases such as asthma, allergic rhinitis, food allergies, atopic dermatitis and anaphylaxis. The alarming increase in the prevalence of allergic diseases over the past decade has led to a clear need for more effective treatment.

The interaction between IgE and mast cells or basophils is the primary effector pathway in allergic responses. IgE binds to high-affinity receptor (FcεRI) for its constant region, found almost exclusively on the surface of these cells. The binding itself, in spite of the low dissociation rate, does not result in stimulation of the cell. However, cross-linkage of cell surface-bound IgE by multivalent antigen causes receptor aggregation, triggering explosive cellular degranulation whereby mediators of allergy such as cellular degranulation whereby mediators of allergy such as histamine and seretonin are released.

The fact that distribution of the FcεRI receptor is restricted to cells participating in an allergic response makes it an attractive candidate for targeted immunotherapy by chimeric cytotoxins. Chimeric cytotoxins are a novel class of targeted molecules constructed by gene fusion techniques. These molecules are composed of cell targeting and cell killing moieties, enabling them to recognize and distroy cells overexpressing specific receptors.

The bacterial toxin Pseudomonas exotoxin (PE) used in chimeric protein constructs, is a product of *Pseudomonas aeruginosa*. Having accessed the cytoplasm, PE inhibits protein synthesis by its ADP-ribosylation activity, thus causing cell death (Middlebrook, J. I., and Dorland, R. B. 1984. Bacterial toxins: cellular mechanisms of action. Microbiol. Rev. 48, 199.). Effective chimeric cytotoxins have been constructed by fusion of cDNAs encoding various growth factors or single chain antibodies with PE derivatives lacking intrinsic cell binding capacity. One of these chimeric proteins designated $IL_2$-$PE_{40}$, constructed to target and selectively eliminate activated T cells overexpressing $IL_2$ receptors, was shown to provide effective and selective immunosuppression in various models of autoimmune disorders, graft rejection and cancer (Lorberboum-Galski, H. 1994. Interleukin 2-Pseudomonas exotoxin A (IL2-PE40) chimeric protein for targeted immunotherapy and the study of immune responses. J. Toxicol.-Toxin Rewiewes, 13 (1), 105.).

The entire recombinant constant region of IgE (Fcε) expressed in bacteria, have an affinity for FcεRI receptor comparable to that of the native IgE, as well as the capacity to sensitize basophils for anti-IgE indused histamine release. When recombinant fragments of human Fcε expressed in bacteria, were tested for receptor binding, a peptide corresponding to residues 301–376 at the junctions of domains 2 and 3 of the constant region was found to be sufficient for high-affinity binding to the receptor. It was also reported that ε-chain dimerization was not required for receptor binding (Helm, B., Marsc, P., Vercelli, D., Padlan, E., Gould, H., and Geha, R. 1988. The mast cell binding site on human immunoglobulin E. Nature 331, 180.).

The present invention generally relates to a novel approach for the therapy of allergic responses. At present the major known groups of drugs used in the treatment of asthma and allergic disorders are:

1. β2 agonists—produce airway dilatation through simulation of β2 adrenergic receptors.
2. Methylxantines—smooth muscle relaxants, produce bronchodilatation.
3. Glucocorticoids—reduce inflammation.
4. Cromolyn sodium—prevents mast cell degranulation.
5. Antihistamines—prevents histamine action on it's target cells.

Although widely used, all of these drugs have notable disadvantages in regard to:

1. Specificity: The action of all of these drugs (except cromolyn sodium) is not mast cell specific. Therefore, they can not prevent the release of allergy mediators but rather reverse or block the effects caused by their action. The treatment by these drugs is symptomatic, it can be started only after the onset of the allergic reaction and thus can't be used in a prophylactic manner.
2. Toxicity: Being non-specific, these drugs exert their action on various tissues and organs causing serious side effects. The major side effect of β2 agonists is tremor, but they also cause cardiac arrhythmias; Methylxantines stimulate the central nervous system, causing nervousness, nausea, vomiting, anorexia, headache and cardiac muscle-causing tachycardia. At high plasma levels there is a danger of seizures and arrhythmias. Antihistamines affect the central nervous system, causing sedation. Steroids are most harmful, causing suppression of the pituitary-adrenal function, fluid and electrolyte disturbances, hypertension, hyperglycemia, increased susceptibility to infections, osteoporosis and arrest of growth in children.
3. Duration of the effect: β-adrenergic agonists, aminoxantines and antihistamines are mostly short-acting drugs, and as such must be administered frequently. Steriods which are long-acting drugs, have also long induction time and are of little value in emergencies.

The only existing mast cell specific drug is Cromolyn sodium. This drug can be used prophilactically, essentially without side effects. However, it has a very short half life, very long induction time, it can be applied only locally and only part of the patients respond to it. All these make use of Cromolyn sodium very limited.

A number of attempts to interfere with interaction between IgE and it's high-affinity receptor, as a basis for anti-allergy therapy, have been reported in recent years. Recombinant peptides comprising structural elements from IgE (Helm, B., Kebo, D., Vercelli, D., Glovsky, M. M., Gould, H., Ishizaka, K., Geha, R., and Ishizaka, T. 1989.

Figure 8:
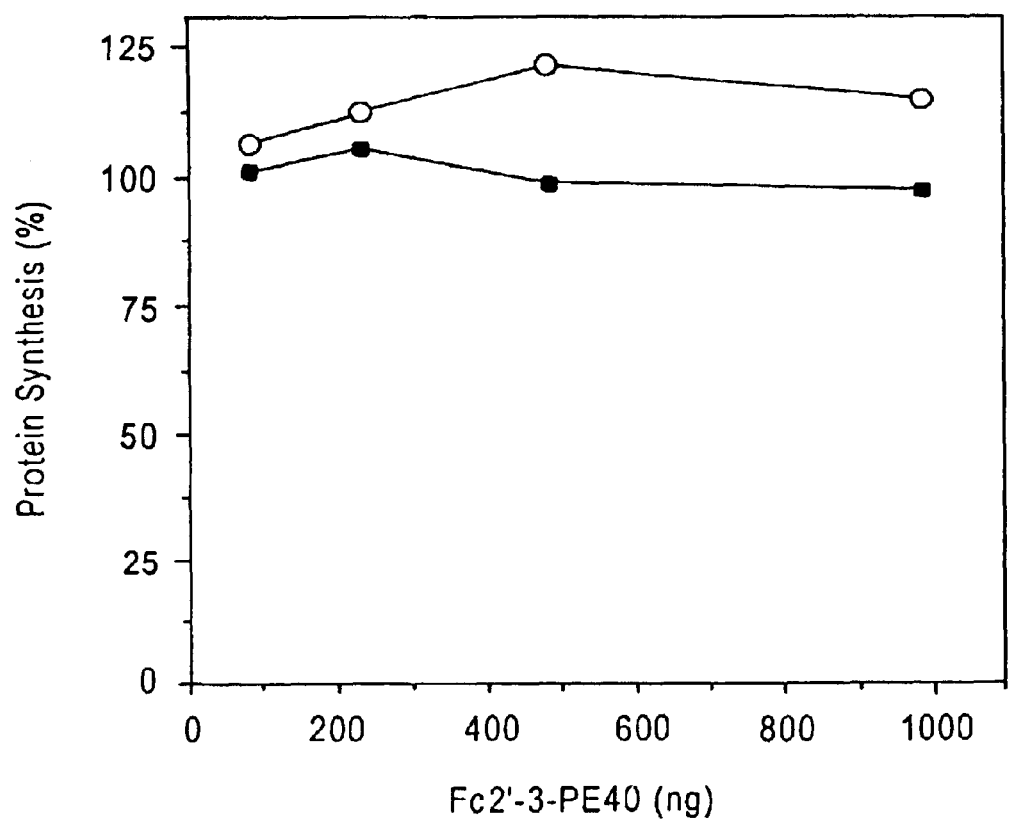

Blocking the passive sensatization of human mast cells and basophil granolocytes with IgE antibodies by a recombinant human ε-chain fragment of 76 amino acids. Proc. Natl. Acad. Sci. USA 86, 9465.) or FCεRI (Ra, C., Kuromitsu, S., Hirose, T., Yasuda, S., Furuichi, K., and Okumura, K. 1993. Soluble human high affinity receptor for IgE abrogates the IgE-mediated allergic reaction. Int. Immunol. 5, 47.; Haak-Frendscho, M., Ridgway, J., Shields, R., Robbins, K., Gorman, C., and Jardieu, P. 1993. Human IgE receptor a-chain IgG chimera blocks passive cutaneous anaphylaxis reaction in vivo. J. Immunol. 151, 351.) have been investigated as competitive inhibitors of the IgE-FcεRI interaction. Monoclonal antibodies generated against IgE (Baniyash, M., and Eshhar, Z. 1984. Inhibition of IgE binding to mast cells and basophils by monoclonal antibodies to murine IgE. Eur. J. Immunol. 14, 799) or FcεRI (Kitani, S., Kraft, D., Fischler, C., Mergenhagen, S. E., and siraganian, R. P. 1988. Inhibition of allergic reactions with monoclonal antibody to the high affinity IgE receptor. J. Immunol. 140, 2585.), capable of blocking IgE binding to the receptor, without causing mast cell degranulation have also been tested. However, the affinity of IgE for FcεRI is very high ($K_M = 10^{-10}$M), so that once it is bound to it's receptor, the IgE molecule remains attached to the cell membrane for several weeks. Moreover, mast cell can be activated at low receptor occupancy: the cross-linkage of as few as 5% of receptors is sufficient to cause mast cell degranulation. These two properties of the system impede inhibition by competitive agents, thus limiting their clinical value. Our anti-allergy molecule depends to a much lesser extent on the ability to compete with IgE. Once having entered the target cell through a non-occupied IgE receptor, the chimeric protein affects the target cell. Moreover, early expression of the receptor in the maturation course of mast calls should allow the elimination of immature target cells before they are capable of mediator release. As the receptor is not expressed on stem cells, no damage to bone marrow is expected on the whole.

The IgE system is quite complex and diverse. Interactions between IgE and its binding structures have many functions apart from the allergic response, some of which are only beginning to emerge. Monoclonal antibodies against IL-4, the IL-4 receptor or the low-affinity IgE receptor eliminate expression of IgE in mice but have more general immunosupressive effects. The advantage of the present invention in which the high-affinity IgE receptor is targeted and not the overall IgE system, is therefore evident.

SUMMARY OF THE INVENTION

The present invention generally relates to a new approach for therapy of allergic responses, based on targeted elimination of cells expressing the FcϵRI receptor by a chimeric cytotoxin $Fc_{2'-3}$-$PE_{40}$. A sequence encoding amino acids 301–437 of the Fc region of the mouse IgE molecule was genetically fused to $PE_{40}$—a truncated form of PE lacking the cell binding domain. The chimeric protein, produced in *E. coli*, specifically and efficiently kills mouse mast cell lines expressing the FcϵRI receptor, as well as primary mast cells derived from bone marrow.

The present invention provides a chimeric protein for targeted elimination of $Fc_{\epsilon}RI$ expressing cells especially usefull for the therapy of allergic responses. The said chimeric protein is comprisesd of a cell targeting moiety for the $Fc_{\epsilon}RI$ expressing cells and a cell killing moiety. The preferred killing moiety is the bacterial toxin Pseudomonas exotoxin (PE). This Pseudomonas exotoxin is a product of *Pseudomonas aeruginosa*.

The present invention also relates to a method for the preparation of said protein. This chimeric protein is prepared by genetically fusing the Fc region of the mouse IgE molecule to $PE_{40}$, a truncated form of PE lacking the cell binding domain.

The present invention also provides a pharmaceutical compositions, for the treatment of allergic diseases and for the treatment of hyperplasias and malignancies, comprising as an active ingredient the above mentioned chimeric protein and a conventional adjuvant product.

The present invention further relates to the method for the preparation of these pharmaceutical compositions comprising genetically fused Fc region of the mouse IgE molecule to $PE_{40}$ and adding, if needed, a conventional adjuvant product. The pharmaceutical compositions according to the present invention may be in any suitable form for injection, for toppical application, or for oral administration.

BRIEF DESCRIPTION OF DRAWINGS

FIG. 1: Schematic representation of plasmids coding for the $Fc_{2'-3}$-$PE_{40}$ and $Fc_{2-4}$-$PE_{40}$ chimeric proteins.

FIG. 2: SDS-polyacryamide gel electrophoresis analysis of cell fractions containing Fcϵ-$PE_{40}$ chimeric proteins. Samples containing 5 μg. total protein were loaded onto 10% gels. (A) Cells expressing $Fc_{2'-3}$-$Pe_{40}$ Lane 1, markers; Lane 2 whole cell extract; Lane 3, soluble fraction; Lane 4, insoluble fraction. (B) Cells expressing $Fc_{2-4}$-$PE_{40}$. Fractions are as described in A.

FIG. 3: Immunobloting of insoluble fractions containing Fcϵ-$PE_{40}$ chimeric proteins with antibodies against PE (A) and IgE (B). Samples containing 1 μg of total protein were loaded onto 10% SDS-polyacrylamide gels. Electrophoressed samples were transferred onto nitrocellulose and processed as described in Materials and Methods. (A) αAPE: Lane 1, $Fc_{2'-3}$-$PE_{40}$; Lane 2: $Fc_{2-4}$-$PE_{40}$ (B) αlgE: Lanes are as described in A.

FIG. 4: Cytotoxic activity of various chimeric proteins against MC-9 cells (A), C57 cells (B), and Abelson cells (C). Cells were incubated for 20 h with insoluble fractions containing the chimeric proteins -■-$Fc_{2'-3}$-$PE_{40}$; -●-$Fc_{2-4}$-$PE_{40}$; -▼-$Fc_{2'-3}$-$PE_{40M}$; or -□-$PE_{40}$ at various concentrations (according to total protein concentration). Experiments with MC-9 cells were performed in the presence of $IL_3$ (20 u/ml) and $IL_4$ (10 u/ml). [$^3$H] Leucine incorporation into cell proteins was measured as described in Materials and Methods. The results are expressed as the percentage of protein synthesis of control cells not exposed to chimeric proteins.

FIG. 5: Inhibition of $Fc_{2'-3}$-$PE_{40}$ cytotoxicity by (A) IgE and (B) αPE. Cells were incubated with whole IgE (40 mg/ml) for 1 h at 4° C. before the addition of $Fc_{2'-3}$-$PE_{40}$ $_{\alpha}$PE (10 mg/ml) was added a few minutes prior to the addition of $Fc_{2'-3}$-$PE_{40}$. All other experimental conditions were as described in FIG. 4. ■

FIG. 6: Cytotoxic activity of various chimeric proteins against bone marrow derived primary mast cells (BMMC). Bone marrow was cultured as described in Materials and Methods. Experiments were performed on the 16$^{th}$ day of culture, as described in FIG. 4, in the presence of $IL_3$ (20 u/ml) and $IL_4$ (10 u/ml).

FIG. 7: Cytotoxic activity of various chimeric proteins against the C57 cells in the presence of: $_{\alpha}$FcγRII/III (2.4G2). Cells were incubated with 2.4G2 (50 μg/ml) or galactose (25 mm) for 30 min. at 37° C. prior to the addition of $Fc_{2'-3}$-$PE_{40}$. All other experimental conditions were as described in FIG. 4. (A) $Fc_{2'-3}$-$PE_{40}$ in the absence (-●-) or presence (-○-) of 2.4G2. (B): $Fc_{2'-3}$-$PE_{40}$ in the absence (-Δ-) or presence (-▼-) of galactose.

FIG. 8: Cytotoxic activity of various chimeric proteins against FcεRII bearing cells. (-○-) B splenocytes. -■- 0.12A3 B cell hybridoma. B splenocytes were preincubated for 16 h. with LPS (50 g/ml) and IL$_4$ (50 u/ml). All other experimental conditions were as described in FIG. 4.

Figure 9A:
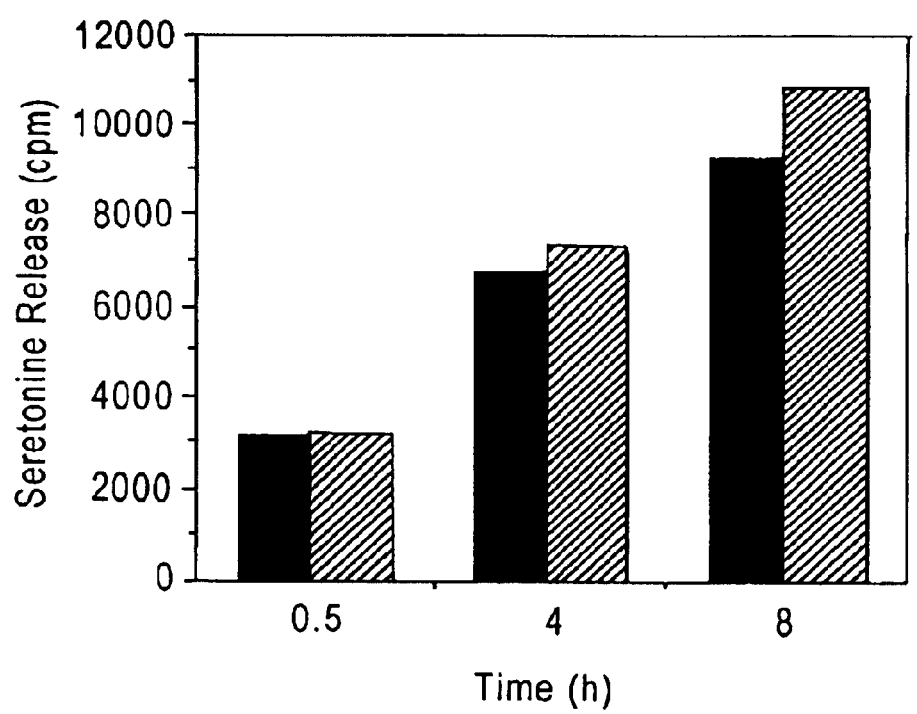

FIG. 9(A): The effect of $Fc_{2'-3}$-$PE_{40}$ on seretonin release from C57 cells. Cells were labeled overnight with [$^3$H] Hydroxytryptamine creatinine sulfate. The cells were then washed and incubated with $Fc_{2'-3}$-$PE_{40}$ (10 µg/ml). Control cells were not exposed to any protein. At different time points [$^3$H] Hydroxytryptamine creatinine sulfate release into the medium was measured. -■-control, -▨-$Fc_{2'-3}$-$PE_{40}$ FIG. 9 (B): Time-dependant cytotoxycity of $Fc_{2'-3}$-$PE_{40}$ against C57 cells. Unlabeled cells were incubated as in (A). At the same time points, cells were pulsed for 1 h with [$^3$H] Leucinie and its incorporation into cellular proteins was measured. The results are expressed as the percentage of protein synthesis of control cells not exposed to chemeric proteins.

Figure 10A:
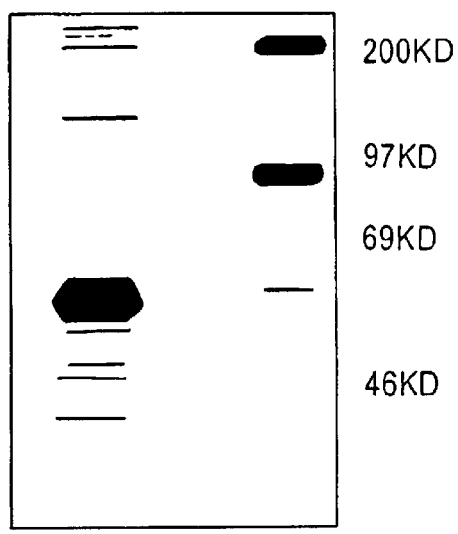
Figure 10B:
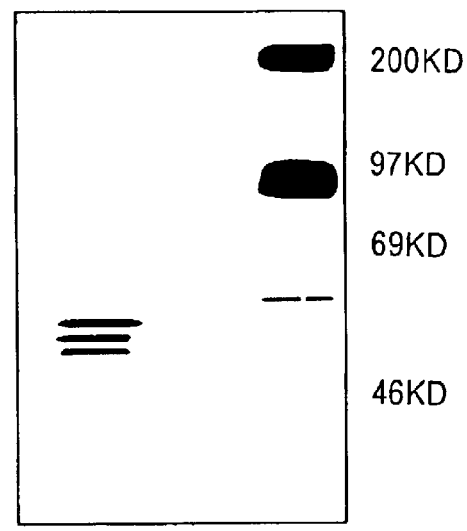

FIG. 10: Immunoblotting of $Fc_{2'-3}$-$PE_{40}$ chimeric protein electrophoresed under the following conditions with anti-PE: A) in SDS under reducing conditions, B) in SDS under nonreducing conditions and C) a nondenaturing gel (i.e. no reduction, no SDS).

Figure 11:
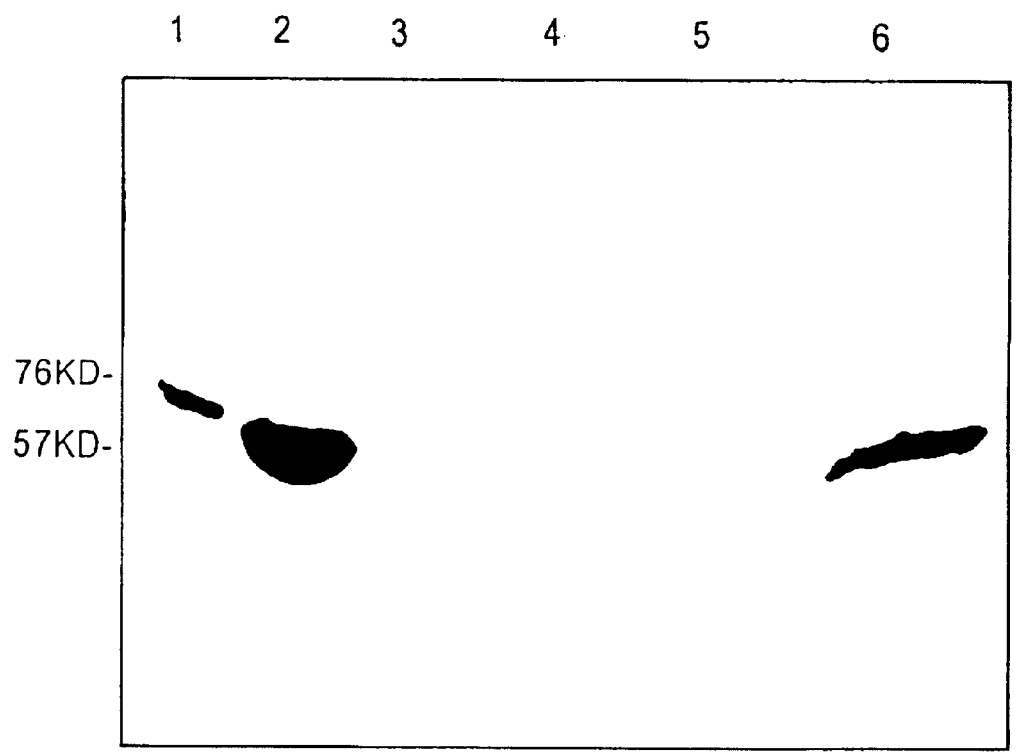

FIG. 11: Internalization of $Fc_{2'-3}$-$PE_{40}$ chimeric protein by MC-9 cells. Samples containing 20 µl of each of the following fractions were loaded onto SDS-10% polyacrylamide gels: lane1. 40 ng $Fc_{2'-3}$-$PE_{40}$; lane 2, supernatant of the cells; lane 3, last wash before the acid treatment; lane 4, acid wash supernatant: lane 5, last wash after acid treatment; and lane 6, lysed cells.

Figure 12A:
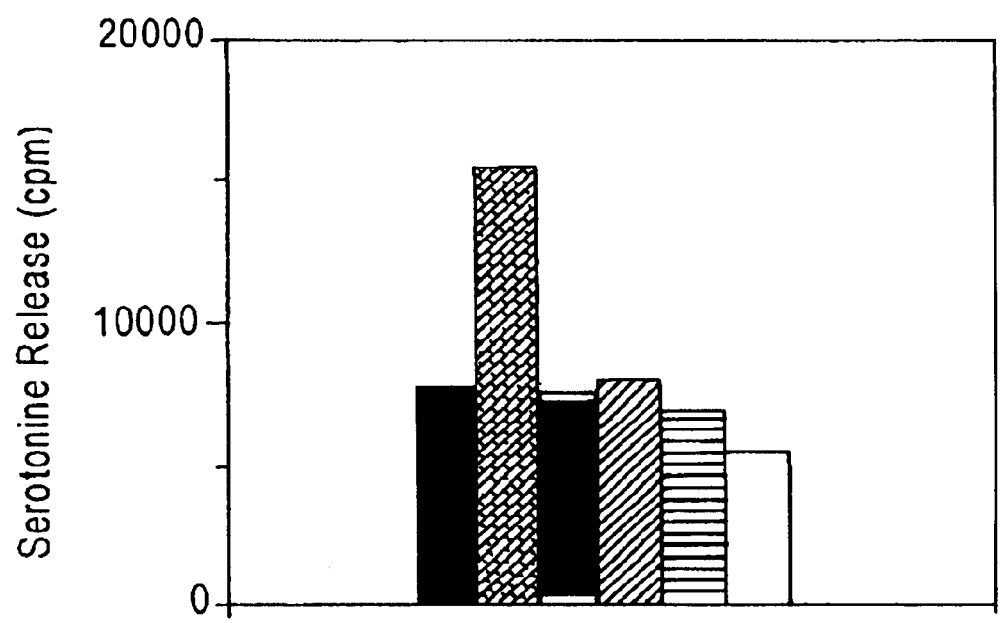

FIG. 12(A): The effect of $Fc_{2'-3}$-$PE_{40}$ on serotonin release from C57 cells. A) Cells were labeled overnight with [$^3$H] hydroxytryptamine creatinine sulfate. The cells were then washed and exposed to various concentrations of $Fc_{2'-3}$-$PE_{40}$ for 30 minutes. Control cells were pre-incubated with IgE and exposed to DNP and [$^3$H] hydroxytyptamine creatinine sulfate released into the medium was measured:

■Control, ▨ IGE-DNP, ■100 ng, ▨ 250,
☰ 1000 ng, or ☐5000 ng $Fc_{2'-3}$-$PE_{40}$ FIG. 12 (B): Cells were incubated with $Fc_{2'-3}$-$PE_{40}$ at different time points [$^3$H] hydroxytryptamine sulfate release into the medium was measured; legends as in FIG. 12(A).

Figure 12B:
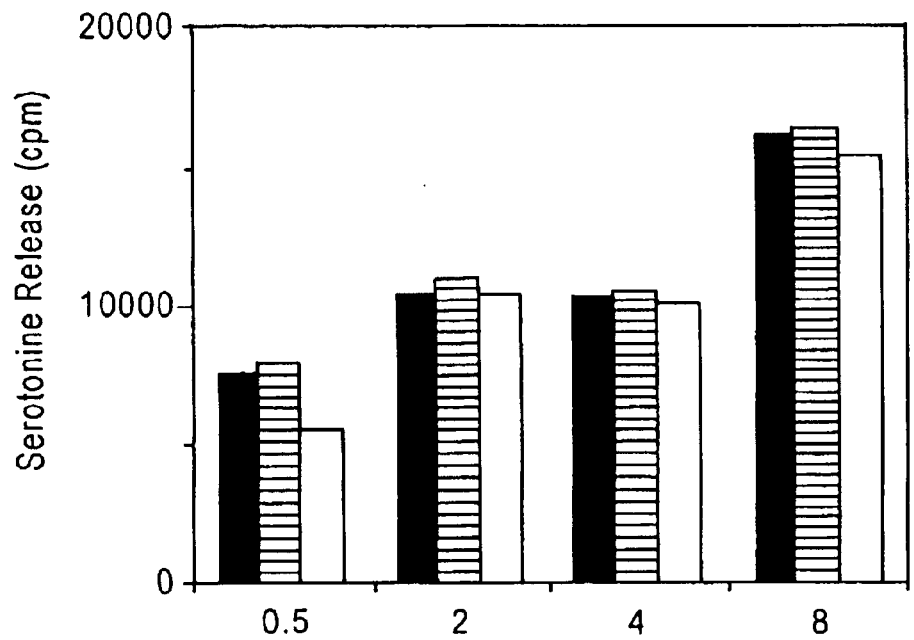

FIG. 12 (C): Time dependent cytotoxicity of $Fc_{2'-3}$-$PE_{40}$ against C57 cells. Unlabeled cells were incubated as in FIG. 12(B). At the same time points cells were pulsed for 1 h with [$^3$H] leucine and its incorporation into cellular proteins was measured. The results are expressed as the percentage of protein synthesis of control cells not exposed to chimeric proteins.

FIG. 13: Table 1: Cytotoxicity of $Fc_{2-3}$-$PE_{40}$ chimeric protein against various mouse cells.

DETAILED DESCRIPTION OF THE INVENTION

The Fc-PE chimeric protein according to the present invention has a number of advantages over the existing known drugs.:

1. Specificity: Fc-PE is highly specific, affecting the cells (mast cells and basophils) responsible for the release of allergic mediators. As it prevents the allergic attack, it can be of great value as a prophylactic treatment.
2. Toxicity: As it acts on affector cells and not on it's target organs, Fc-PE is expected to have little, if any, side effects. Moreover, as the receptor is not expressed on stem cells, no damage to bone marrow and immunosupression are anticipated. Re-institution of a normal psysiological state is expected to occur within several weeks after the end of the treatment.
3. Duration of the effect: Because maturation of mast cells takes several weeks, the effect of Fc-PE is predicted to be long-standing, eliminating the need for frequent administration. Moreover, as in vitro studies indicate that reduction of 80% in cellular protein systhesis is observed in less than 4 hours, induction time of Fc-PE is expected to be relatively short, enabling it's usage in acute phase allergic reactions.

Fcε-PE can also be valuable in the treatment of hyperplasias and malignancies of mast cells and basophils, like systemic mastocytosis (in both benign and malignant forms) and basophilic leukemia. Chemotherapy is not appropriate for patients with benign mastocytosis due to severe side effects. On the other hand, there is no good clinical protocol for the treatment of the malignant diseases. Fcε-PE chimeric protein, being highly potent and selective can be used for both benign and malignant conditions involving cells expressing the FcεRI receptors.

The following experimental results indicate that the $Fc_{2'-3}$-$_{PE}40$chimeric protein according to the present invention is a promising candidate for effective and selective allergy therapy.

The present invention provides a Fcε-PE chimeric cytotoxin protein for the targered elimination of FcεRI expressing cells, useful especially for the therapy of allergic responses such as asthma, allergic rhinitis, food allergies, atopic dermatitis, and anaphylaxis.

The said invention will be further described in detail by the following experiments. These experiments do not intend to limit the scope of the invention but to demonstrate and clarify it only.

1. Construction of Fcε-$PE_{40}$ Chimeric Proteins.

For the targeting moiety of the chimeric proteins fragments of the mouse IgE constant region (Fcε) are used as it binds both to human and to mouse high affinity IgE receptors (Conrad, D. H., Wingard, J. R., and Ishizaka, T. 1983 The interaction of human and rodent IgE with the human basophil IgE receptor. J. Immunol. 130, 327.).

We used a sequence corresponding to a.a. 301–437, containing the COOH terminus of domain 2 and the entire domain 3($C_2'$–$C_3$). We used also a sequence corresponding to a.a. 225–552, containing the whole $C_2$–$C_4$domains. The cDNA for these fragments was obtained by RT-PCR, using RNA isolated from mouse B cells which were isotopically switched to secrete IgE and a specific set of primers. B cells obtained from the spleen of a 6-week-old BALB/C mouse were separated by negative selection using anti-Thy1.2 and rabbit complement. Cells were incubated at 2×10$^6$ cells/ml in the presence of Lipopolysaccharide (LPS, 10 µg/ml) and IL$_4$ (500 u/ml) for 5 days to induce isotypic switching for IgE production. After 5 days, total cellular RNA was isolated (RNAzol TM B isolation kit produced by BIOTECK Laboratories, Houston, USA.). Total RNA (2.5 µg) was then reverse transcribed into first strand cDNA, using the reverse transcription System (Promega, USA) under conditions, recomended by the manfacturer. The cDNA was diluted to a total volume of 1 ml with TE buffer (10 mM Tris-HCL, pH 7.6, 1 mM EDTA) and stored at 4° C. until used.

Fcε fragments were generated by PCR, using cDNA and a pair of synthetic oligonucleotide primers 5'-GCG GAT CCC ATA TGG AGC AAT GGA TGT CGT-3', SEQ ID NO. 5, (sense, starting from nucleotide 406, according to gene bank sequence J00476) and 5'-GCG CCC ATA TGT GGG GTC TTG GTG ATG GAA C-3', SEQ. ID NO. 6, (antisense, starting from nucleotide 813) for the Fc$\epsilon_{2-3}$ sequence and 5'-GCG GAT CCC ATA TGC GAC CTG TCA ACA TCA CTG-3', SEQ. ID. NO. 7, (sense, starting from nucleotide 175) and 5'-GCG GAT CCC ATA TGG GAG GGA CGG AGG GAG G-3', SEQ. ID. NO. 8, (antisense, starting from nucleotide 1167) for the Fc$\epsilon_{2-4}$ sequence.

Synthetic oligonucleotides were synthesized on an Applied Biosystems DNA synthesizer and purified on oligonucleotide purification cartridges. The vent polymerase enzyme (Biolabs) was used for amplification. The reaction mixture was incubated in a DNA thermal cycler (MJ Research, Inc, USA.) for 33 cycles. Each cycle consisted of 1 min. at 95° C., 1 min. at the annealing temperature and 2 min. at 72° C. The MgSO$_4$ concentration and the annealing temperature used for each primer pair were: 2.5 mM and 61° C. for Fc$_{2'-3}$', 2 mM and 57° C. for Fc$_{2-4}$.

The pHL 906 plasmid, which encodes IL$_2$-PE$_{40}$, was described previously (Fishman, A., Bar-Kana, Y., Steinberger, I., and Lorberboum-Galski, H. 1994. Increased cytotoxicity of IL2-PE chimeric proteins containing targeting signal for lysosomal membranes. Biochem. 33, 6235.). The pHL906 plasmid was cut with NdeI, obtaining the larger fragment of 3596 bp. The above Fcε fragment was inserted into the NdeI site of pHL906. The resulting plasmids, pAF2302 and pAF2415, coding for the C$_1$'–C$_3$ and C$_2$–C$_4$ fragments respectivly, each fused 5' to PE$_{40}$, were characterized by restriction and sequence analysis (results not shown). *Escherichia coli* strain HB101 was used for transformation and preparation of the plasmids.

2. Expression and Partial Purification of the Chimeric Proteins.

Figure 1A:
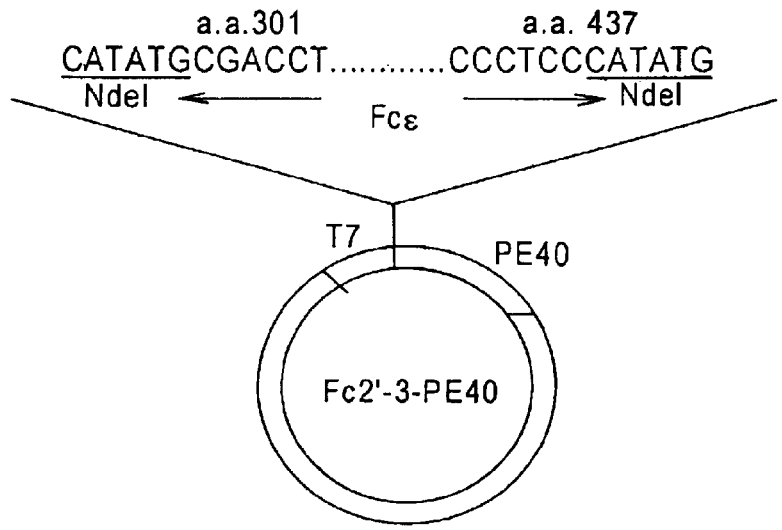
Figure 1B:
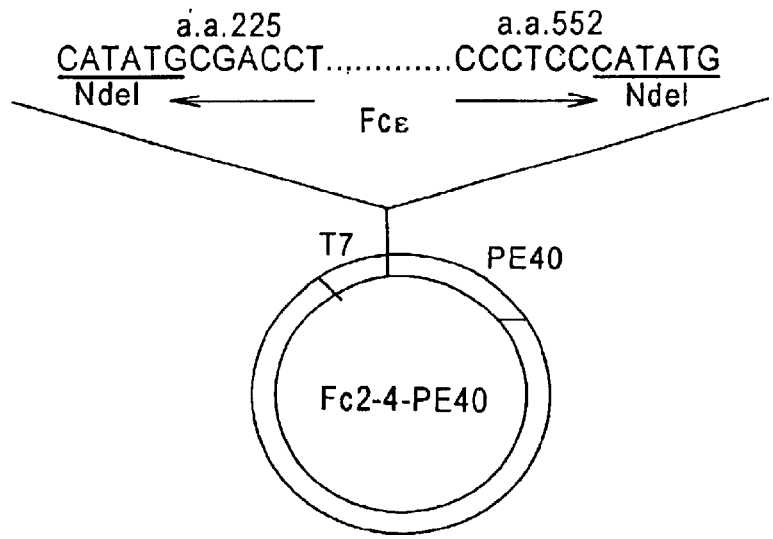
Figure 2A:
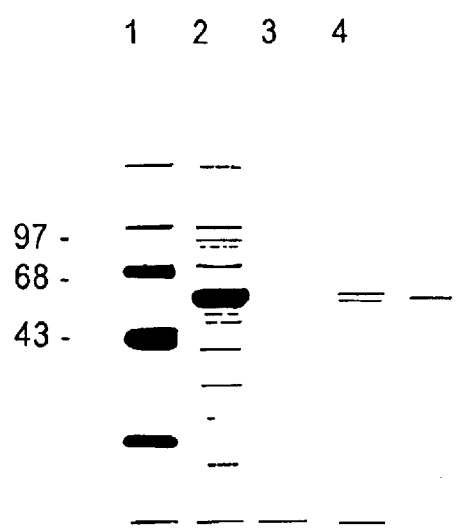
Figure 2B:

The newly designed chimeric protein, Fcε-PE$_{40}$ encoded by plasmid pAF2302 was expressed in *E. coli* strain BL21 (lambda-DE3) which carries a T7 RNA polymerase gene in a lysogenic and inducible form. Induction was performed at O.D.d.$_{600}$0.5 for 180 min. in the presence of isopropyl β-D-thiogalactoside (IPTG, 1 mM final concentration). A pellet expressing cells was suspended in TE buffer (50 mM Tris pH 8.0, 1 mM EDTA) containing 0.2 mg/ml lysosyme, sonicated (three 30s bursts) and centrifuged at 30,000×g for 30 min. The supernatant (soluble fraction) was removed and kept for analysis. The pellet was denatured in extraction buffer (6 M guanidine-hydrochloride, 0.1 M Tris pH 8.6, 1 mM EDTA, 0.05 M NaCl and 10 mM DTT) and stirred for 30 min. at 4° C. The suspension was cleared by centrifugation at 30,000×g for 15 min. and the pellet discarded. The supernatant was then dialysed against 0.1 M Tris (pH 8.0), 1 mM EDTA, 0.25 mM NaCl and 0.25 mM L-Arginine for 16 h. The dialysate was centrifuged at 15,000×g for 15 min. and the resultant supernatant (insoluble fraction, guanidine-hydrochloride treated) was used as a source of the chimeric proteins. Proteins were characterized by gel electrophoresis (FIG. 2). The protein profile of whole cell extracts revealed the high expression level of the chimeric protein.

Figure 3A:
Figure 3B:

The protein was further characterized by Western blot analysis using antibodies against PE (FIG. 3A) and against IgE (Serotec, England) (FIG. 3B). The electrophoresed samples were transfered onto nitrocellulose and immunoblotted as described (Lorberboum-Galski, H., Fitzgerald, D. J., Chaudhary, V., Ashya, S., and Pastan, I. 1988. Cytotoxic activity of an interleukin 2—Pseudomonas exotoxin chimeric protein produced in *Escherichia coli*. Proc. Natl. Acad. Sci. USA 85, 1992.). A Vectastain ABC Kit (Vector Laboratories, USA) was used according to the manufacturer's instructions. The chimera reacted with both antibodies, thus confirming the cloning and production of in-frame full-length chimeric protein.

Subcellular fractionation of expressing cells revealed that the insoluble fraction (inclusion bodies) was paticularly rich with chimeric protein (FIG. 2). This fraction was therefore used as the source of the chimeric protein.

The ADP-ribosylation activity of tested samples was measured using wheat germ extracts enriched in elongation factor 2 as substrate, as described previously, and revealed that the novel chimeric protein was enzymatically active (results not shown).

3. Effect of Fc$_{2'-3}$-PE$_{40}$ Chimeric Protein on Mouse Mast Cell Lines.

The cytotoxic effect of the chimeric protein was tested on various mouse mast cell lines known to express the Fc$_\epsilon$RI receptor. The cytotoxic activity of the chimeric protein was evaluated by inhibition of protein synthesis, as measured by [$^3$H] Leucine incorporation. Various concentrations of the chimeric protein, diluted with 0.25% bovine serum albumim in phosphate-buffered saline, were added to 2×10$^4$ cells/0.2 ml seeded in 96-well plates for 20 h., followed by an 8 h pulse with 2 μCi of [$^3$H]-Leucine. The results are expressed as a percentage of the control experiments in which the cells were not exposed to the chimeric protein. All assays were carried out in triplicate in three separate experiments.

Figure 4A:
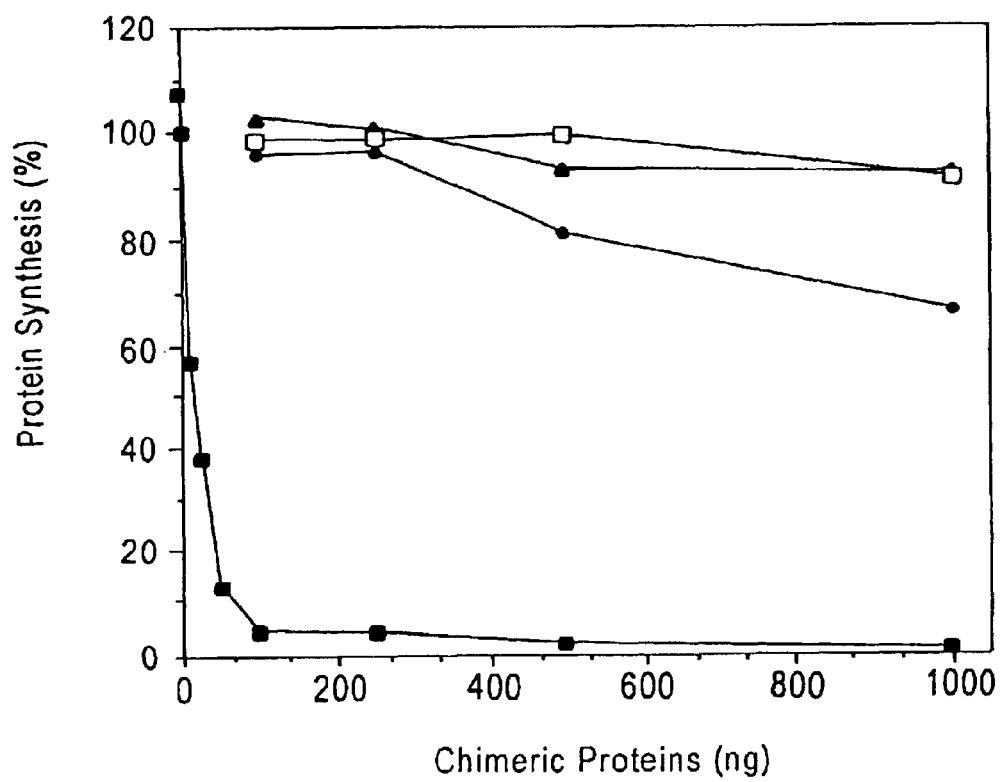
Figure 4B:
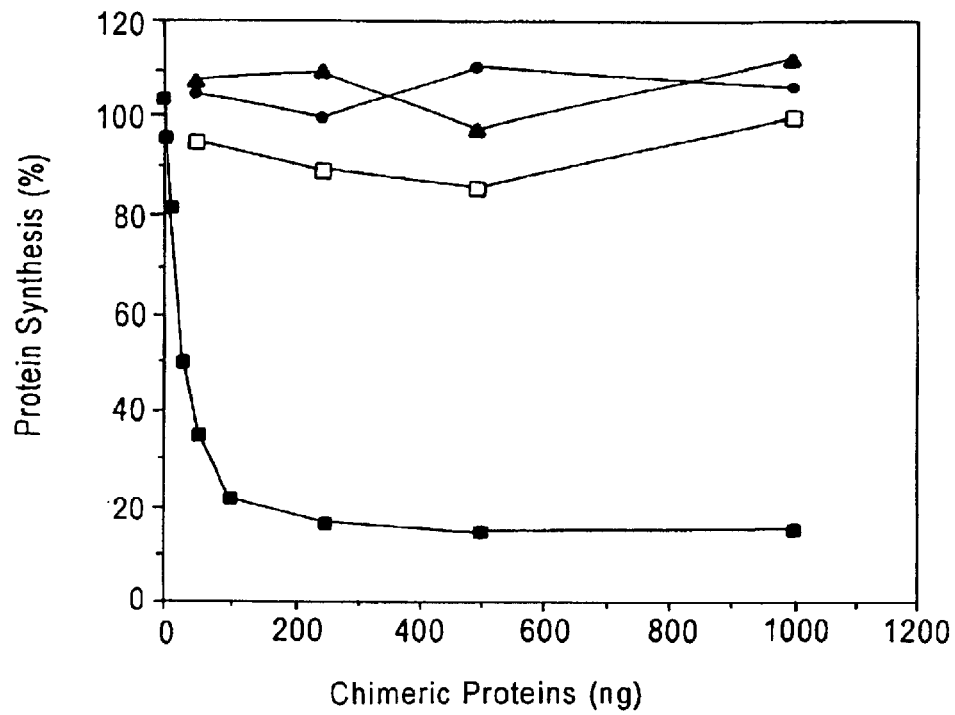
Figure 4C:
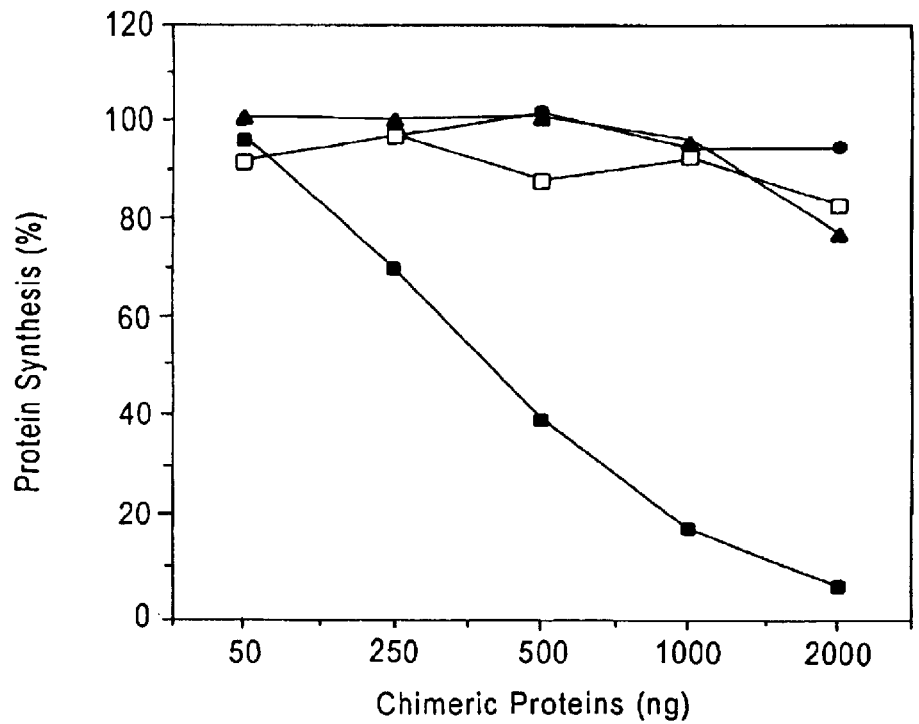

Three target cell lines expressing the FcεRI receptor were used: MC-9, a mast cell line originating in mouse fetal liver and dependent on IL$_3$ for growth, C57, an IL$_3$ independent mast cell line originating in mouse bone marrow; and the Abelson-virus transformed mast cell line originating in mouse midgestation embryonic placenta. Fcε-PE$_{40}$ was found to be cytotoxic in a dose-dependent manner to all the cell lines tested (FIG. 4). The MC-9 and C57 lines were extremely sensitive to the chimeric toxin, with an ID$_{50}$ of 50–75 ng/ml and 100–125 ng/ml, respectively. The Alelson cell line was much less sensitive (ID$_{50}$ of 1200–1500 ng/ml).

4. Specificity of Fcε-PE$_{40}$ Response.

To verify the specificity of Fc$_{2'-3}$-PE$_{40}$ activity, two control proteins, PE$_{40}$ and Fc$_{2'-3}$-PE$_{40M}$, were generated and evaluated for their effect on target and non target cells. To construct Fc$_{2'-3}$-PE$_{40M}$, the region coding for the 122 amino acids at the C-terminal of PE was exised with EcoRI and BamHI and replaced by a corresponding fragment carrying a deletion at amino acid 553.

PE$_{40}$, which has no intrinsic targeting capacity had, as expected, no effect on the target cell lines (FIG. 4). Fc$_{2'-3}$-PE$_{40M}$ which possesses a Fc$_{2'-3}$ moiety linked to a mutated, enzymatically inactive form PE$_{40}$, was also not cytotoxic to the target cells (FIG. 4).

Figure 5A:
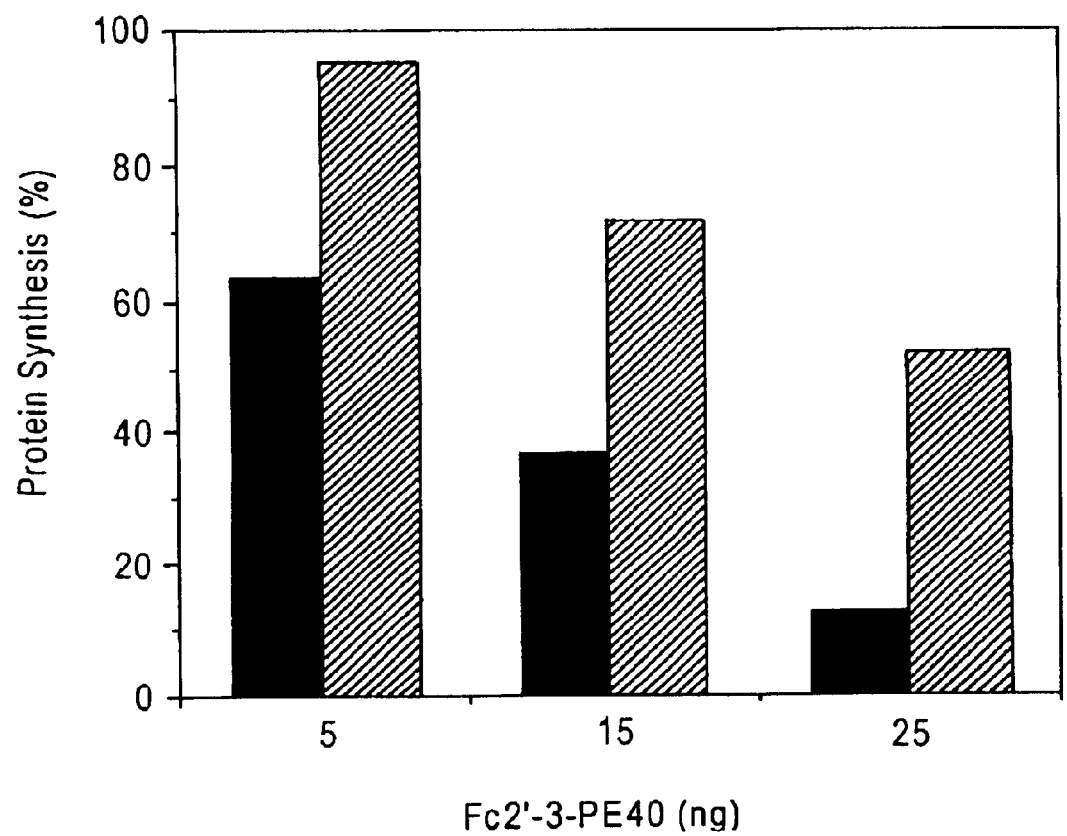
Figure 5B:
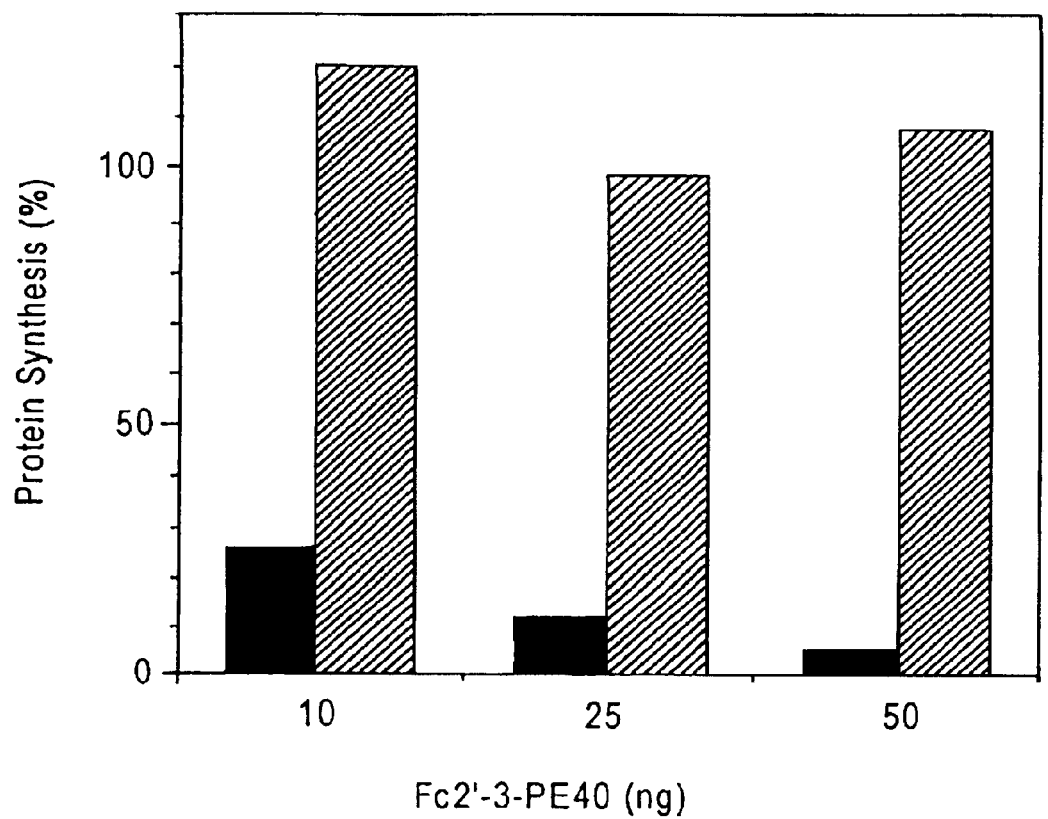

In addition, it was possible to block the cytotoxic effect of Fc$_{2'-3}$-PE$_{40}$ against target cells by whole mouse IgE (40 μ/ml, FIG. 5A) or by a αPE polyclonal antibody (10 μg/ml, FIG. 5B).

The effect of Fc$_{2'-3}$-PE$_{40}$ was also tested on various mouse non-target cell lines (Table 1). All cell lines of hemopoetic origin were unaffected by the chimeric protein. Suprisingly, fibroblast and hematoma cell lines exhibited some sensitivity to chimeric toxin, although the ID$_{50}$ values were twenty-fold higher than those of the MC-9 cells (Table 1).

The above data demonstrates that the toxic effect of Fc$_2$'-3-$_{PE}$40 on mast cell lines is due to a specific response mediated by the Fc$_{2'-3}$ moiety which targets the cytotoxic part of the chimera (PE$_{40}$) into the cell.

5. Effect of Chimeric Proteins on Primary Mast Cells.

As it is likely that fresh murine mast cells react differently from established cell lines, we also tested primary mast cells obtained from normal mice for their sensitivity to Fc$_{2'-3}$-PE$_{40}$. When cultured in the presence of IL$_3$ for two weeks, mouse bone marrow differentiates into an almost pure population of cells with the morphology of immature mast cells, containing granules and expressing the FcεRI receptor.

BALB/C mice aged 4–6 weeks were sacrificed and their bone marrow was aseptically flushed from femurs into 0.9% cold NaCl. The cell suspension was washed twice with 0.9% Nacl, centrifuged for 10 min. at 300×g and finally resuspended in RPMI 1640 medium containing 10% heat inactivated fetal calf serum, 4 mM L-glutamine, 1 mm sodium piruvate, 0.1 mM nonessential amino acids, $5 \times 10^{-5}$ M β-mercaptoethanol, 100 u/ml penicillin, 100 μg/ml streptomycin and 20 u/ml recombinant mouse $IL_3$. Cells were grown in tissue culture flasks at a density of $10^6$ cells/ml, at 37° C. in a 5% $CO_2$ humidified atmosphere for 2–3 weeks. The media were changed every 7 days. Recombinant $IL_4$ (10 u/ml) was added starting from day 7 in culture.

To follow the degree of maturation, cells were mounted on slides, stained with acidic Toluidine Blue (pH 1.0) and examined microscopically under oil.

Figure 6:
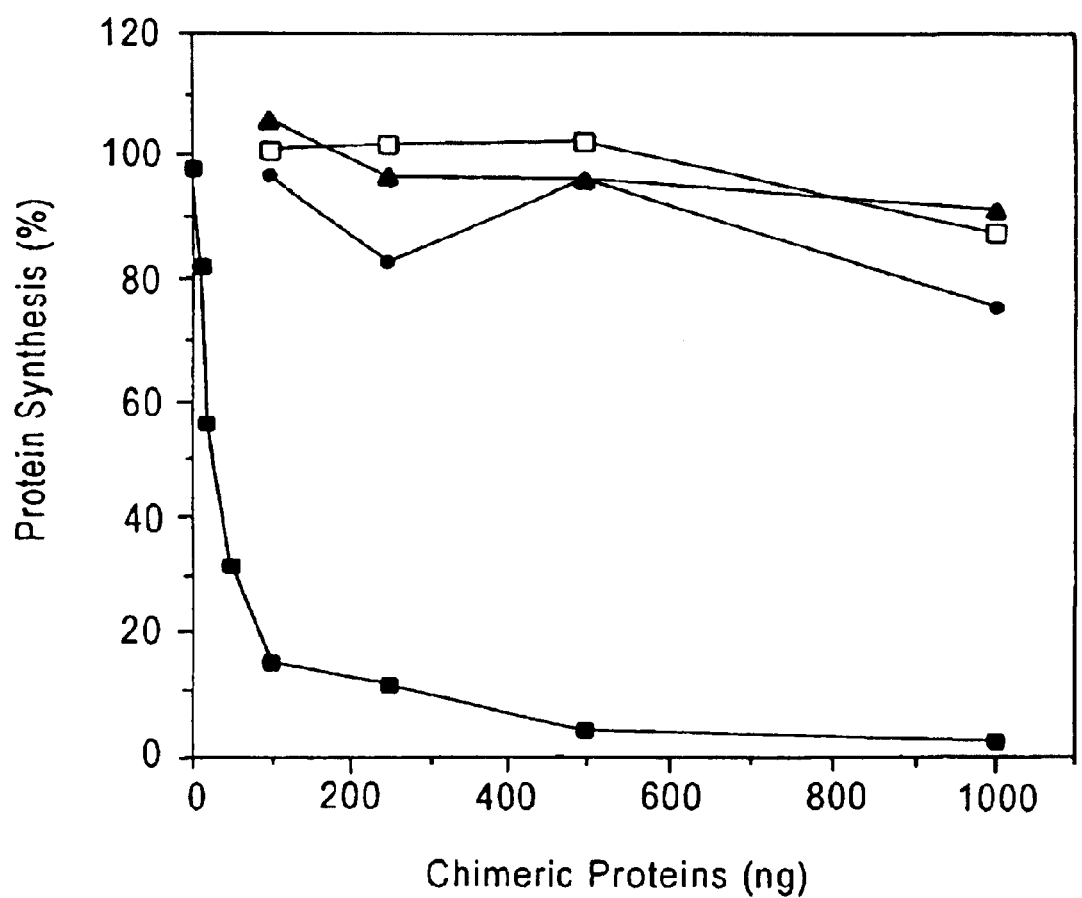

The effect of chimeric proteins was tested on bone marrow derived mast cells (BMMC) on the 16th day of culture. As shown in FIG. 6, $Fc_{2'-3}$-$PE_{40}$ was cytotoxic to BMMC in a dose dependent manner, with an $ID_{50}$ of 125 ng/ml. At a high chimeric protein dose, there was nearly 100% inhibition of protein synthesis. None of the control proteins $Fc_{2'-3}$-$PE_{40M}$ or $PE_{40}$ displayed cytotoxicity against BMMC (FIG. 6). Thus, primary mast cells respond towards the chimeric protein similarly to the established mast cell lines (FIG. 4 and 6).

6. Receptor Specificity of $Fc_{2'-3}$-$PE_{40}$.

Aside from the high affinity $Fc_\epsilon RI$ receptor, three other membrane surface structures were reported to bind IgE with low affinity—the low affinity $Fc_\epsilon RII$ receptor, the εBP galactoside-binding protein (also termed MAC-2 or CBP35) and the FcγRII/III receptor. These structures appear on various cell types, mainly of hemopoethic origin, but also on fibroblasts (εBP). FcγRII/III and εBP appear on mast cell membranes in addition to FcεRI. As our aim was to target only mast cells, it was essential to prove that the chimeric protein does not recognize these structures and thus can not be internalized through them. Theoretically our chimeric protein does not fulfill the binding requirements of the low-affinity IgE binding structure FcεRII, εBP and FcγRII/III. FcεRII binds only disulfide linked ε-chain dimmers, while our protein lacks domain 4 which is essential for dimerization. εBP binds only glycosylated IgE; $Fc_{2'-3}$-$PE_{40}$ being produced in bacteria, is not glycosylated. FcγRII/III binds IgE-immunocomplexes but not free IgE. Nevertheless, the issue of receptor binding was challenged experimentally.

Figure 7A:
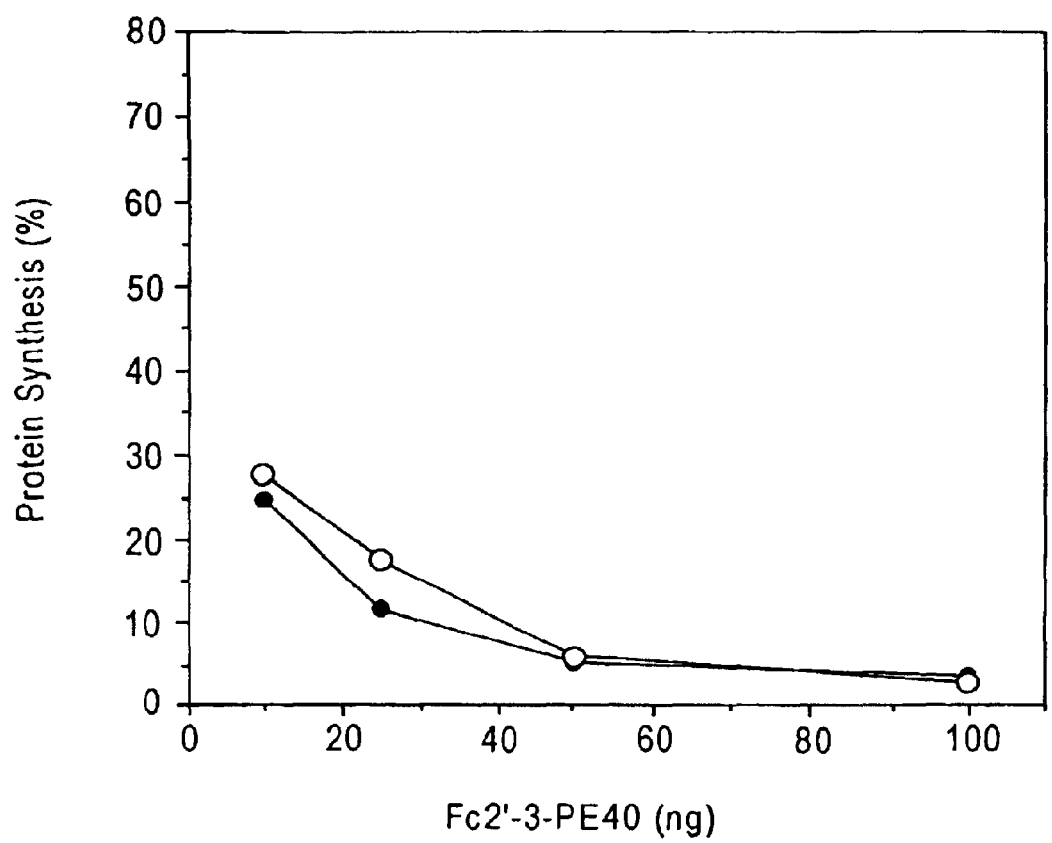

Experiments involving εBP and FcγRII/III were performed on C57 mast cells, known to express these receptors in addition to FcεRI. To test whether the chimeric protein can enter the cell via the FcγRII/III receptors, cells were preincubated with the 2.4G2 antibody (Pharmigen) (50 μg/m) prior to addition of the chimeric protein. This monoclonal antibody, which binds to the extracellular domains of both FcγRII and the FcγRIII receptors was shown to be a competitive inhibitor of IgE binding. As can be seen in FIG. 7A, there was no difference in the cellular response to $Fc_{2'-3}$-$PE_{40}$ between control cells and cells preincubated with the antibody.

Figure 7B:
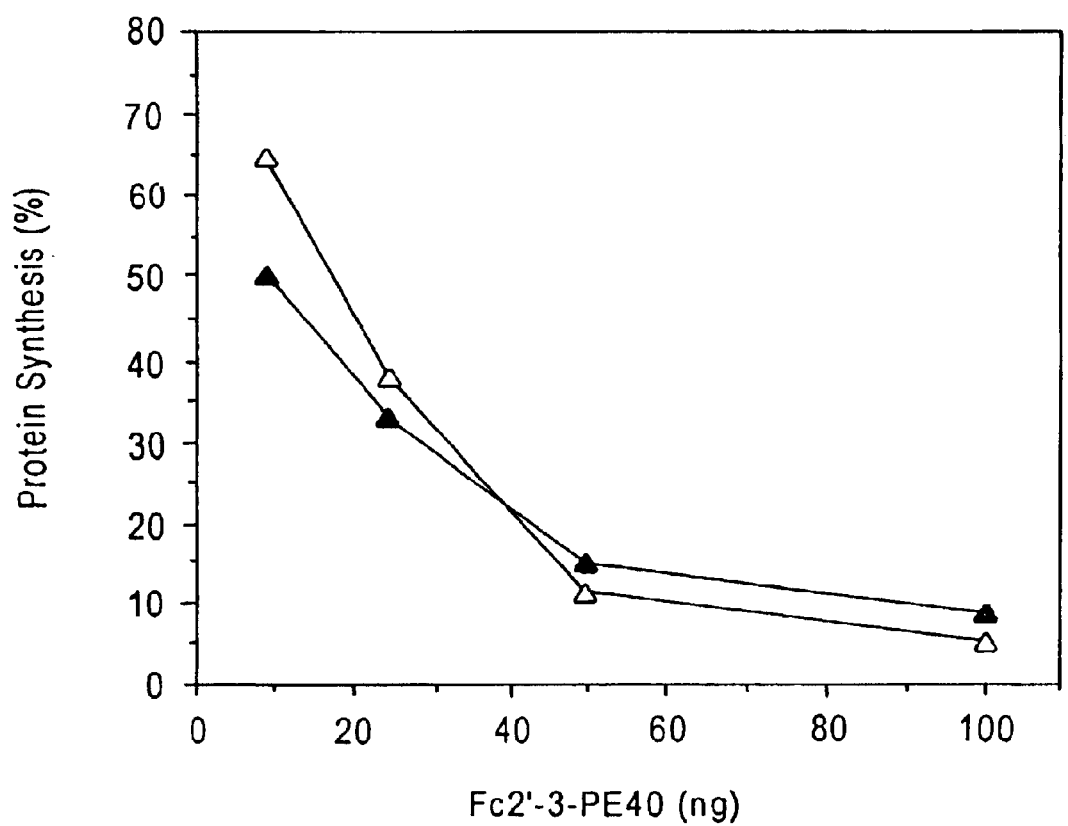

We next examined whether εBP is involved in the cytotoxicity of $Fc_{2'-3}$-$PE_{40}$. As εBP is attached to membrane carbohydrate determinants, addition of lactose to the culture medium causes its dissociation from the cell surface. We found no difference in the cellular response to $Fc_{2'-3}$-$PE_{40}$ in the presence or absence of lactose (25 mM, FIG. 7B).

Additional experiments in the presence of 2.4G2 antibody and lactose were performed on fibroblast cell lines that were found partially responsive to the chimeric protein (Table 1). Again, there was no difference in $Fc_{2'-3}$-$PE_{40}$ cytotoxicity against treated and control cells (results not shown).

To test whether $Fc_{2'-3}$-$PE_{40}$ affects $Fc_\epsilon RII$-bearing cells, we used the 0.12A3 cell line, a mouse B cell hybridoma expressing the $Fc_\epsilon RII$ receptor. The 0.12A3 cells were totally non responsive to $Fc_{2'-3}$-$PE_{40}$, even at high doses (>5000 ng/ml, FIG. 8A). As this line loses the receptor upon long term culture, the assay was followed by FACS analysis with the B3B4 antibody against the receptor (Pharmigin). The results showed that the receptor was expressed on 54% of the cells (results not shown).

An additional experiment was performed on fresh mouse B splenocytes preincubated for 16 h. with LPS (50 μg/ml) to stimulate expression of FcεRII. $Fc_{2'-3}$-$PE_{40}$ has no effect on these B splenocytes (FIG. 8B), although 69% of the cells expressed the receptor, as determined by FACS analysis.

Collectively, these results suggest that $Fc_{2'-3}$-$PE_{40}$ does not bind to the low affinity IgE-binding structures, namely $Fc_\epsilon RII$, FcγRII/III and εBP.

7. Effect of $Fc_{2'-3}$-$PE_{40}$ on Cellular Degranulation.

Figure 9B:
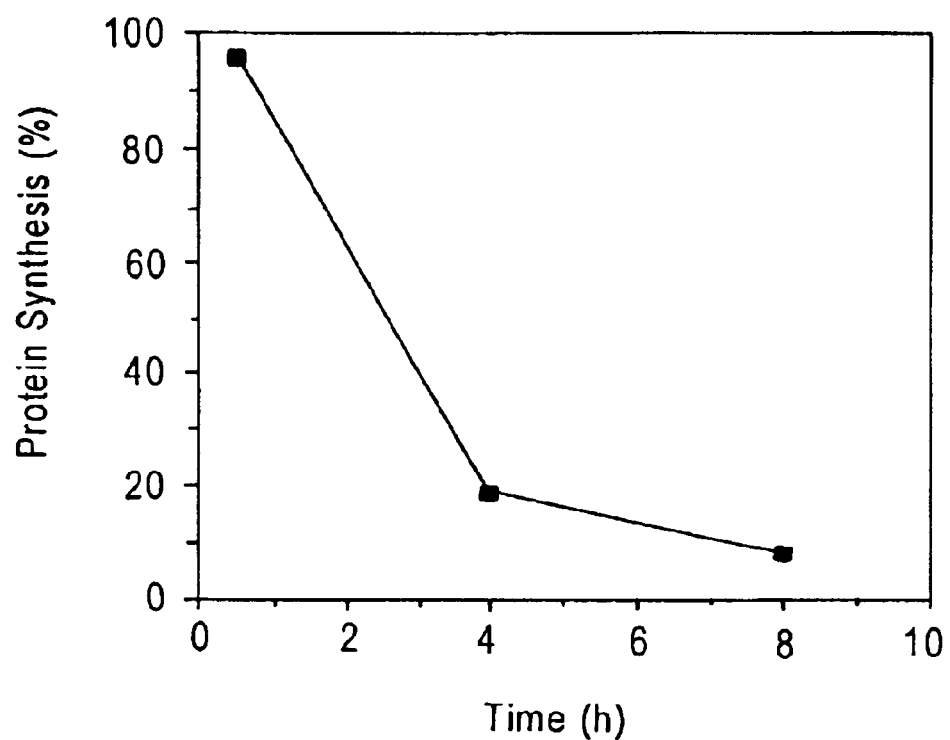

Because of the possible clinical applicability of $Fc_{2'-3}$-$PE_{40}$, it was important to test whether treatment of mast cells with $Fc_{2'-3}$-$PE_{40}$ results in the release of allergic mediators triggered upon $Fc_\epsilon RI$ binding by the chimetric protein. C57 cells prelabelled overnight with $[^3H]$-hydroxytryptamine 10 μci/ml) were washed, plated at $2 \times 10^5$ cells/well in DMEM containing 10% FCS, in 96-well tissue culture plates and incubated with $Fc_{2'-3}$-$PE_{40}$ (10 μg/ml) at 37° C. At various time points, supernatants were separated and release of seretonin into the supernatant was measured. Unlabled cells were also incubated with $Fc_{2'-3}$-$PE_{40}$ and at the same time intervals were pulsed 1 hr with $[^3H]$ leucine to measure protein systhesis inhibition by chimeric toxin. There was no difference in supernatant $[^3H]$ seretonin content between $Fc_{2'-3}$-$PE_{40}$ treated and untreated cells at ½4 or 8 hr following chimeric protein addition (FIG. 9A). Inhibition of protein synthesis reached 80% at 4 h. and a value of 90% by 8 h. (FIG. 9B). These results suggest that $Fc_{2'-3}$-$PE_{40}$ does not cause release of allergic mediators during receptor binding or upon inhibition of protein synthesis.

8. Electrophoretic Characterization of Fcε-PE40

Figure 10C:
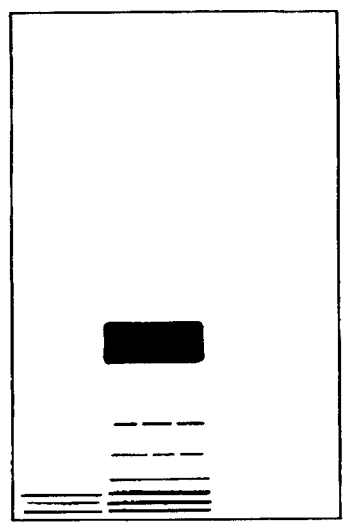

Western blot analysis of electrophoresed samples run under non-reducing conditions (omitting 2-mercaptoethanol from the sample buffer) revealed that the Fc2'-3-PE40 chimeric protein is predominantly present as a monomer (figure lob). For native PAGE, 2-mercaptoethanol was omitted from the sample buffer and the samples were not heated. In addition, SDS was replaced with equivalent volumes of water in the gel, sample buffer and electrode running buffer. Under non-denaturing conditions the chimeric protein runs as a broad band (FIG. 10c). A single native system can not distinguish the effects of molecular weight, charge and conformation on protein electrophoretic mobilities. However, the proximity of the molecules in the band indicates that they can not differ much in these parameters.

9. Internalization Assay

In vitro activity of the chimeric protein is achieved only upon it's internalization. To test whether the chimeric protein is internalysed, $5 \times 10^5$ cells/3 ml were incubated for 1 hour with 20 μg of the chimeric protein at 37° C. After 3 washes with cold PBS the pellet was treated with 0.5 ml of acid solution (0.15M NaCl, 0.15M acetic acid (pH 3)) for 3 min on ice to remove membrane-bounded chimeric protein. The pH was then neutrilised by addition of 50% FCS following by three washed with RPMI/10% FCS. The cell pellet was lysed with 0.3 ml of RIPA lysis buffer (150 mM NaCl, 1 mM EDTA, 20 mM tris-HCl pH 7.4, 1 mM phenylmethylsulfonyl fluoride, 15% SDS, 1% deoxycholyc acid, 1% Nonidet P-40). Various samples were electrophoresed and immunoblotted using α-PE and the ECL detection system (Amersham). Western blot analysis revealed undoubtfully that Fc2'-3-PE40 chimeric protein is internalized into the target cells (FIG. 11).

10. Effect of $Fc_{2'-3}$-$PE_{40}$ on Cellular Degranulation

Figure 12C:
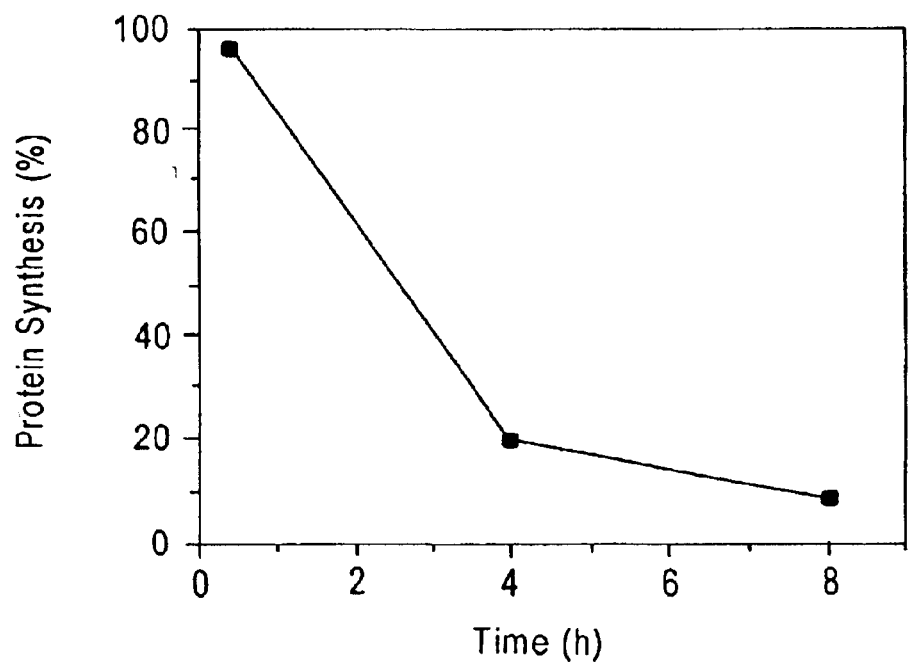

C57 cells were incubated overnight with [$^3$H]-Hydroxytryptamine (10 μci/ml) at 37° C. Cells were washed 3 times to remove free [$^3$H]-Hydroxytryptamine, plated in Tyrod's buffer (10 mM Hepes pH 7.4, 130 mM. NaCl, 5 mM KCl, 5.6 mM Glucose, 0.5% BSA) at $2.5 \times 10^5$ cells/0.5 ml in 24 well tissue culture plates and incubated with IgE (10 μg/ml) for 1 hour at 4° C. $MgCl_2$ and $CaCl_2$ were then added to the final concentration of 1 mM and 1.6 mM respectively, following by incubation with Dinitrophenyl-human serum albumin (DNP-HSA, 50 ng/ml) for 30 minutes or with the different concentrations of chimeric protein for various times at 37° C. Cell-free supernatants were collected by centrifugation and amount of [$^3$H]-Hydroxytryptamine released was measured. No degranulation was observed with any concentration of chimeric protein tested (FIG. 12a). As a control, cells preincubated with IgE were exposed to DNP under the same conditions. The effect of triggering degranulation by DNP is clearly visible (FIG. 12a). $Fc_{2'-3}$-$PE_{40}$ did not cause any degranulation also at later stages of it's interaction with the target cell (FIG. 12b), while it inhibits protein synthesis by over 80% (FIG. 12c). Our results demonstrate that $Fc_{2'-3}$-$PE_{40}$ does not trigger degranulation at any stage during it's interaction with the cell.

What is claimed is:

1. A chimeric protein for therapy of allergic responses by targeted elimination of $Fc_\epsilon RI$ expressing cells; wherein said chimeric protein is comprised of a cell targeting moiety comprising an Fc region of a mouse IgE molecule; and a cell killing moiety.

2. A chimeric protein according to claim 1 wherein the killing moiety is the bacterial toxin Pseudomonas exotoxin (PE).

3. A chimeric protein according to claim 1 wherein the cell targeting and cell killing moieties are genetically fused.

4. A chimeric protein according to claim 1 wherein a sequence encoding amino acids 225–552 of the Fc region of the mouse IgE molecule is genetically fused to $PE_{40}$, a truncated form of PE lacking the cell binding domain.

5. A chimeric protein according to claim 1 wherein a sequence encoding amino acids 301–437 of the Fc region of the mouse IgE molecule is genetically fused to $PE_{40}$, a truncated form of PE lacking the cell binding domain.

6. Pharmaceutical compositions for the treatment of allergic diseases and for the treatment of hyperplasias and malignancies evolving cells expressing $Fc_\epsilon RI$ receptor comprising of an active ingredient a chimeric protein as defined in claim 1 and a conventional adjuvant product.

7. A pharmaceutical composition for the treatment of allergic diseases and for the treatment of hyperplasias and malignancies according to claim 6 wherein said composition is in a suitable form for injection (intra-veneous, intra-articular, sub-cutaneous, intra-muscular, intra-peritoneal), intra-nasal, intra-thecal, intra-dermal, trans-dermal, inhalation, toppical application, oral administration, sustained release, or by any other route including the enteral route.

* * * * *